(12) United States Patent
Gleeson et al.

(10) Patent No.: US 7,388,096 B2
(45) Date of Patent: Jun. 17, 2008

(54) CRYSTALLINE FORMS OF A FACTOR XA INHIBITOR

(75) Inventors: Margaret M. Gleeson, Monmouth Junction, NJ (US); Gary McGeorge, Franklin Park, NJ (US); Bang-Chi Chen, Plainsboro, NJ (US); Huiping Zhang, Belle Mead, NJ (US); Mary F. Malley, Lawrenceville, NJ (US); John D. DiMarco, East Brunswick, NJ (US); Denette K. Murphy, Princeton, NJ (US); Xiaotian Yin, Plainsboro, NJ (US); Steven R. Fabian, Barnegat, NJ (US); Jasmine M. Gupta, Monmouth Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 376 days.

(21) Appl. No.: 11/235,519

(22) Filed: Sep. 26, 2005

(65) Prior Publication Data

US 2006/0069118 A1    Mar. 30, 2006

Related U.S. Application Data

(60) Provisional application No. 60/613,656, filed on Sep. 28, 2004.

(51) Int. Cl.
  *C07D 471/02* (2006.01)
  *C07D 491/02* (2006.01)
  *C07D 498/02* (2006.01)
  *C07D 513/02* (2006.01)
  *C07D 515/02* (2006.01)
(52) U.S. Cl. .................................... 546/120

(58) Field of Classification Search ............... 546/120; 514/303
See application file for complete search history.

(56) References Cited

U.S. PATENT DOCUMENTS

| | | | |
|---|---|---|---|
| 6,967,208 B2 | 11/2005 | Pinto et al. | |
| 2004/0220174 A1 | 11/2004 | Pinto et al. | |
| 2005/0124602 A1 | 6/2005 | Pinto et al. | |
| 2005/0171085 A1 | 8/2005 | Pinto et al. | |
| 2005/0261287 A1 | 11/2005 | Pinto et al. | |
| 2005/0267097 A1 | 12/2005 | Pinto et al. | |
| 2006/0069119 A1* | 3/2006 | Mudryk et al. | 514/303 |

FOREIGN PATENT DOCUMENTS

WO      WO 0326652      4/2003

OTHER PUBLICATIONS

Pedersen et al., The journal of biological chemistry, vol. 265, pp. 16786-16793.*
Elodi et al., "Optimization of conditions for the catalytic effect of the factor IXa-factor VIII Complex: Probable role of the complex in the amplification of blood coagulation", Thromb. Res., vol. 15, pp. 617-629, 1979.

* cited by examiner

*Primary Examiner*—Margaret D. Seaman
*Assistant Examiner*—Niloofar Rahmani
(74) *Attorney, Agent, or Firm*—Jing G. Sun

(57) ABSTRACT

The instant invention provides crystalline forms of 1-(3-chlorophenyl)-7-oxo-6-[4-(2-oxo-1 (2H)pyridinyl)phenyl]-4,5,6,7-tetrahydro-1H-pyrazolo[3,4-c]pyridine-3-carboxamide and its solvates thereof; processes for the production of such crystalline forms; pharmaceutical compositions comprising such crystalline forms; and methods of treating thromboembolic disorders with such crystalline forms or such pharmaceutical compositions.

22 Claims, 17 Drawing Sheets

* indicates spinning sidebands (artifacts)

CRYSTALLINE FORMS OF A FACTOR XA INHIBITOR

CROSS-REFERENCE TO RELATED APPLICATIONS

The present application claims the priority benefit of U.S. Provisional Application No. 60/613,656 filed Sep. 28, 2004, the entire disclosure of which is herein incorporated by reference.

FIELD OF THE INVENTION

The present invention relates to crystalline forms of 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide and its solvates thereof; processes for the production thereof; pharmaceutical compositions thereof; and methods of treating thromboembolic disorders, therewith.

BACKGROUND OF THE INVENTION

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617-629), inhibition of factor Xa may be more efficient than inactivation of thrombin in interrupting the blood coagulation system.

U.S. Patent Application Publication No. 2003/0191115, which is herein incorporated by reference, discloses 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide (hereinafter referred to as "Compound (I)"):

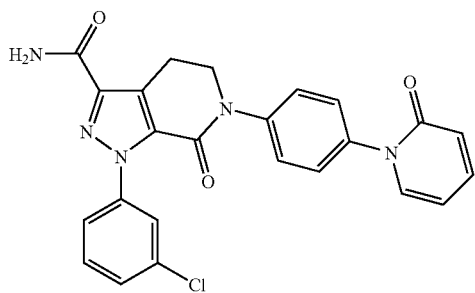

(I)

Compound (I) is a highly potent and selective inhibitor of coagulation Factor Xa and thus is useful in preventing or treating thromboembolic disorders.

Treatment or prevention of the foregoing disorders may be accomplished by administering a therapeutically effective amount of Compound (I) to a human or animal subject in need of such treatment or prevention. The treatment with Compound (I) may be accomplished by its use as a single compound, as a pharmaceutical composition ingredient, or in combination with other therapeutic agents. Compound (I) may be administered by oral administration, continuous intravenous infusion, bolus intravenous administration or any other suitable route such that it preferably achieves the desired effect of preventing the Factor Xa induced formation of thrombin from prothrombin.

Crystalline forms of Compound (I) have not been known to exist previously. There exists a need for crystalline forms which may exhibit desirable and beneficial chemical and physical properties. There also exists a need for reliable and reproducible methods for the manufacture, purification, and formulation of Compound (I) to permit its feasible commercialization. The present invention is directed to these, as well as other important aspects.

SUMMARY OF THE INVENTION

The present invention provides crystalline forms of Compound (I):

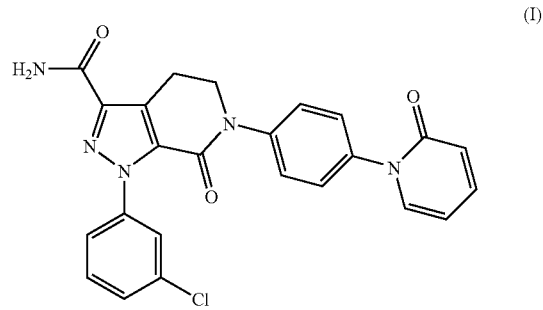

(I)

processes for the production of such forms; pharmaceutical compositions comprising such forms; and methods of treating thromboembolic disorders with such crystalline forms, or such pharmaceutical compositions. Embodiments of these crystalline forms include those characterized herein as Forms N-3, N-1 and N-2, 0.5SBu-4 and Phases P-1 and P-3. The names used herein to characterize a specific form, e.g. "N-3" etc., should not be considered limiting with respect to any other substance possessing similar or identical physical and chemical characteristics, but rather it should be understood that these designations are mere identifiers that should be interpreted according to the characterization information also presented herein.

These and other aspects of the invention will become more apparent from the following detailed description.

BRIEF DESCRIPTION OF THE DRAWINGS

The invention is illustrated by reference to the accompanying drawings described below.

λ=1.5418 Å) of Form N-1 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 4:
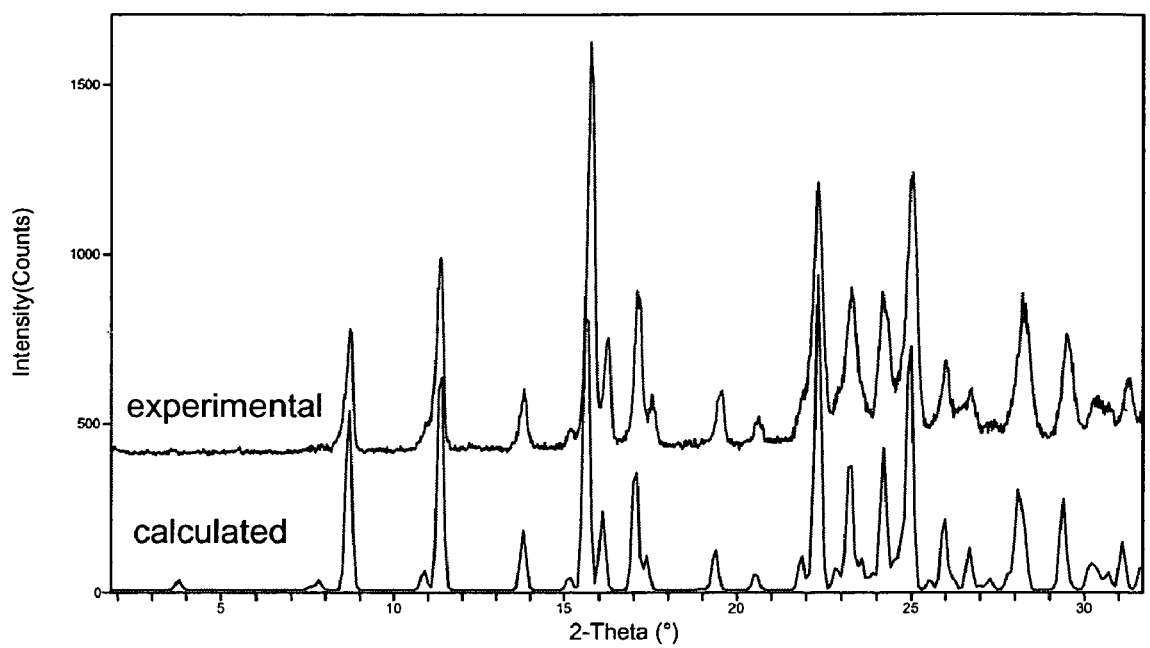

FIG. 4 shows calculated (22° C.) and experimental (room temperature) powder X-ray diffraction patterns (CuKα λ=1.5418 Å) of Form N-2 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 5:
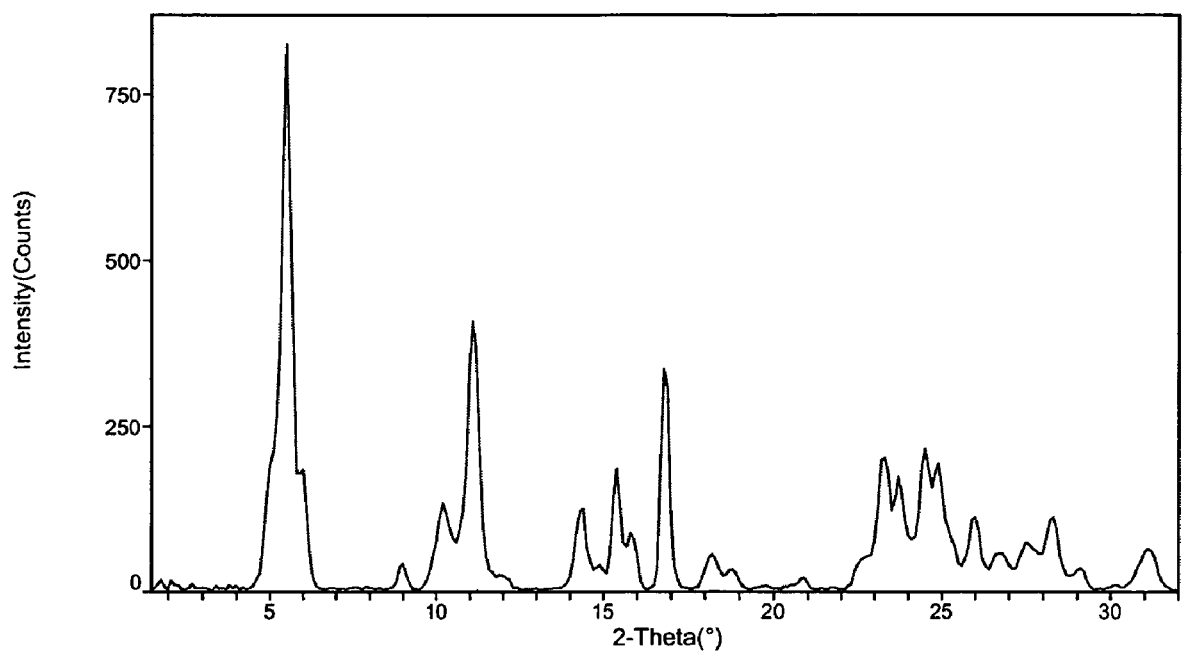

FIG. 5 shows observed (room temperature) powder X-ray diffraction pattern (CuKα λ=1.5418 Å) of Phase P-1 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 6:
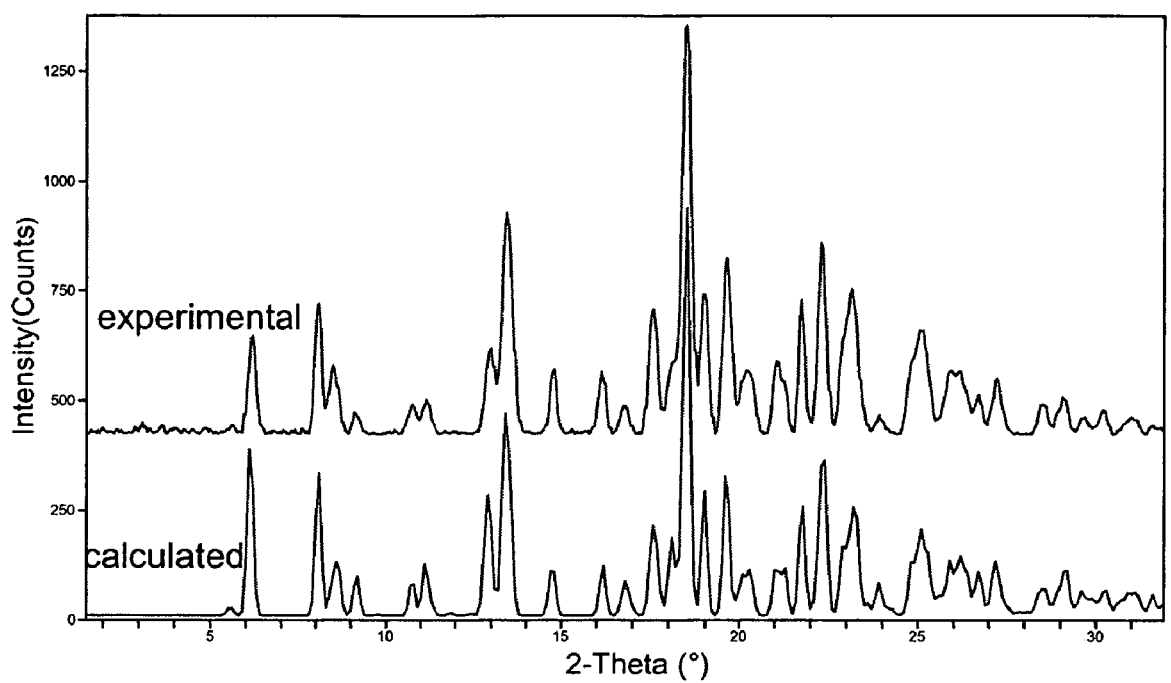

FIG. 6 shows calculated (22° C.) and experimental (room temperature) powder X-ray diffraction patterns (CuKα λ=1.5418 Å) of Form 0.5S-Bu-4 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 7:
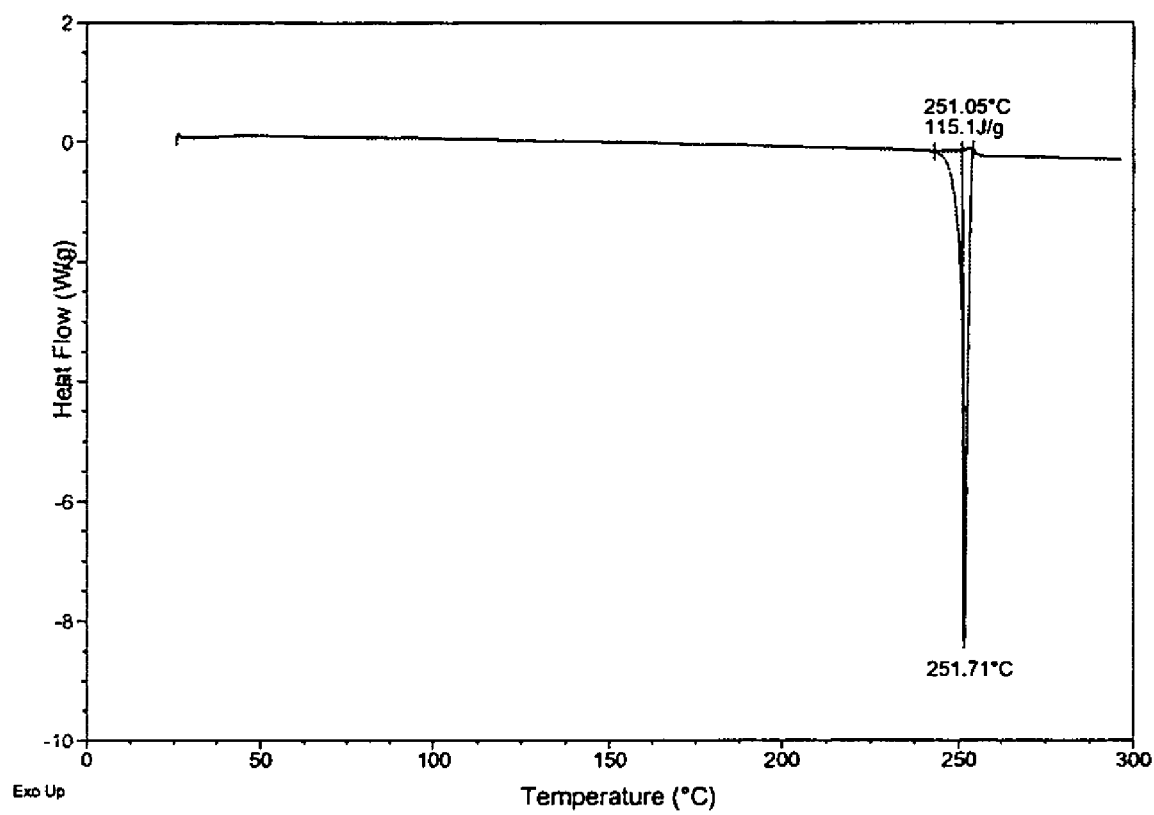

FIG. 7 shows differential scanning calorimetry thermogram of Form N-3 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 8:
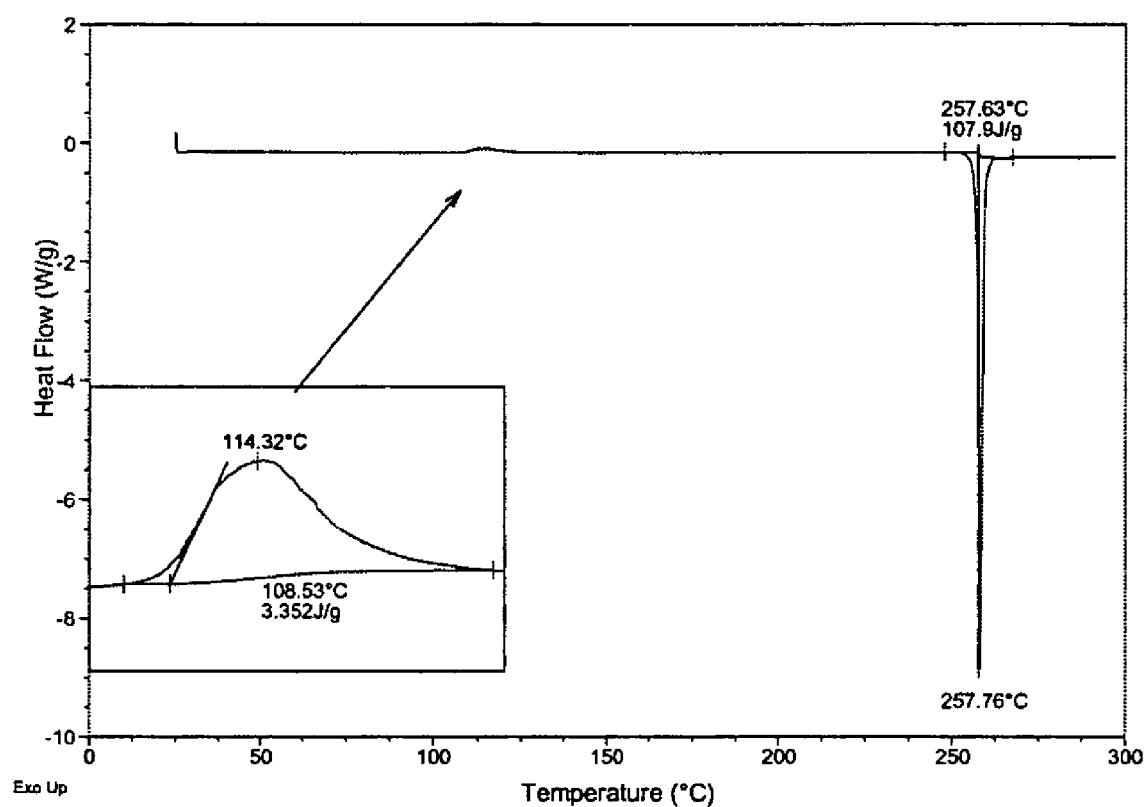

FIG. 8 shows differential scanning calorimetry thermogram of Form N-1 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 9:
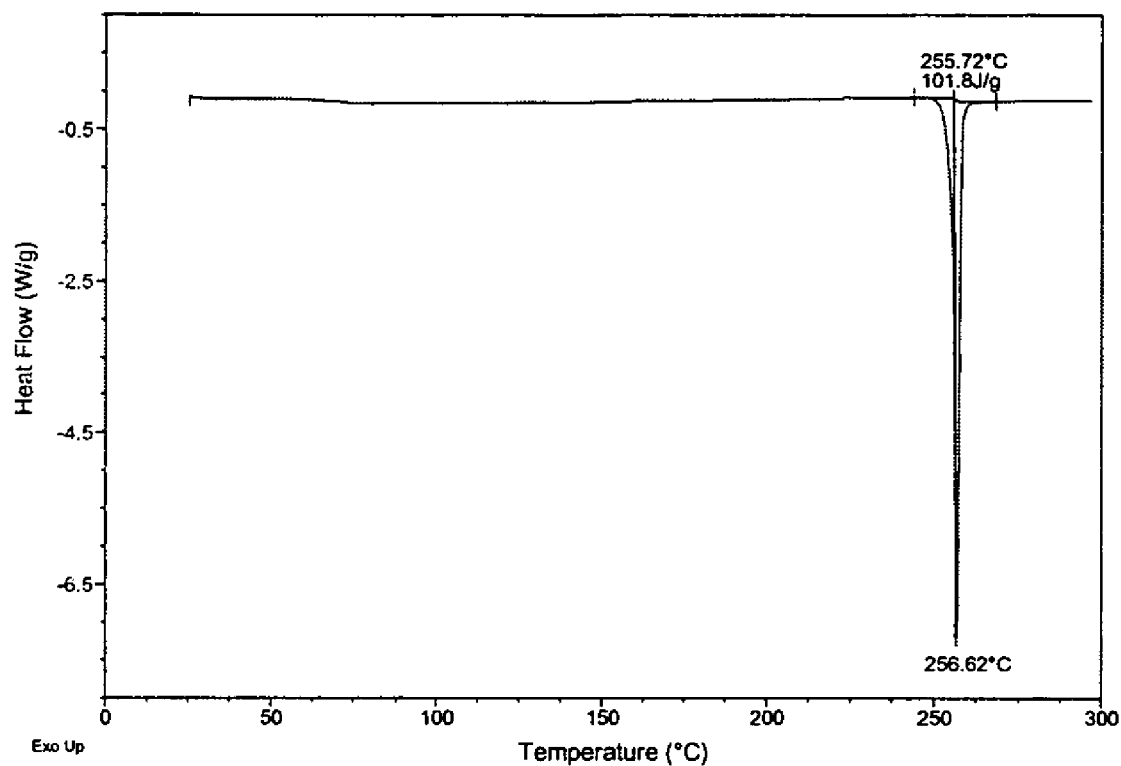

FIG. 9 shows differential scanning calorimetry thermogram of Form N-2 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 10:
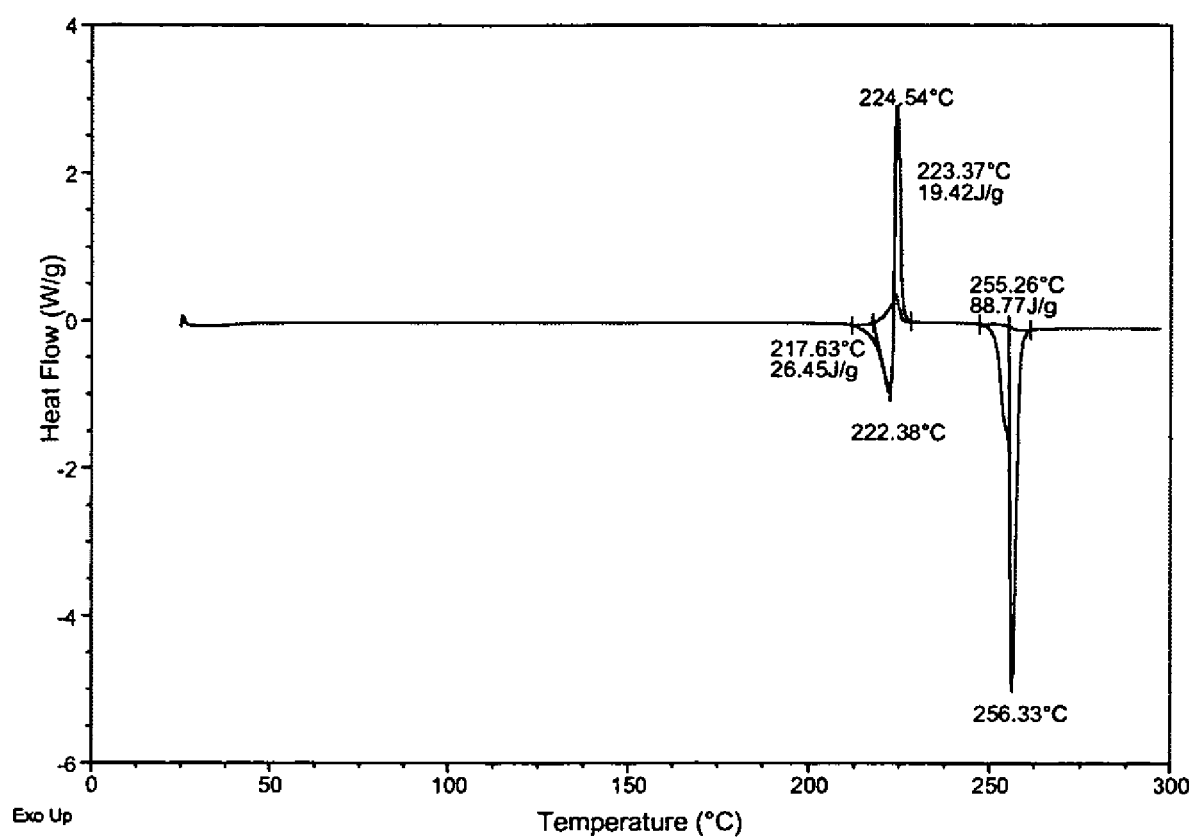

FIG. 10 shows differential scanning calorimetry thermogram of Phase P-1 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 11:
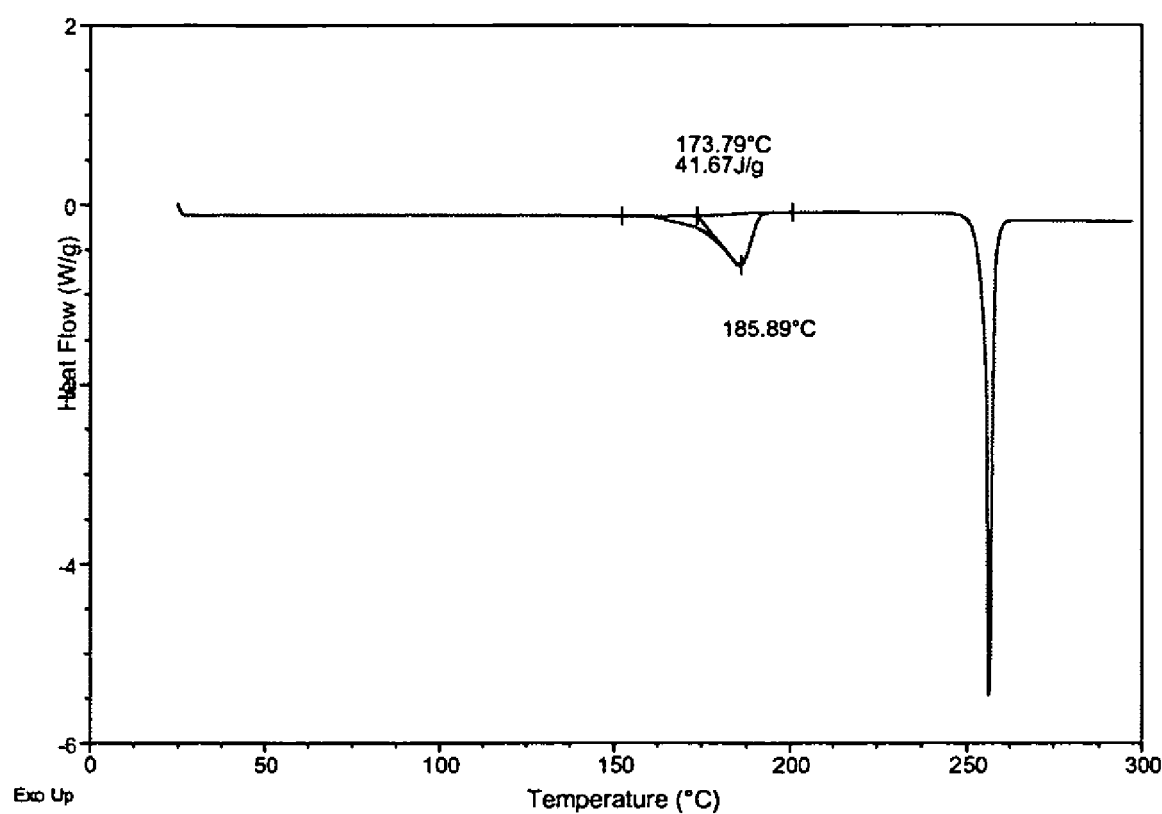

FIG. 11 shows differential scanning calorimetry thermogram of Form 0.5 SBu-4 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 12:
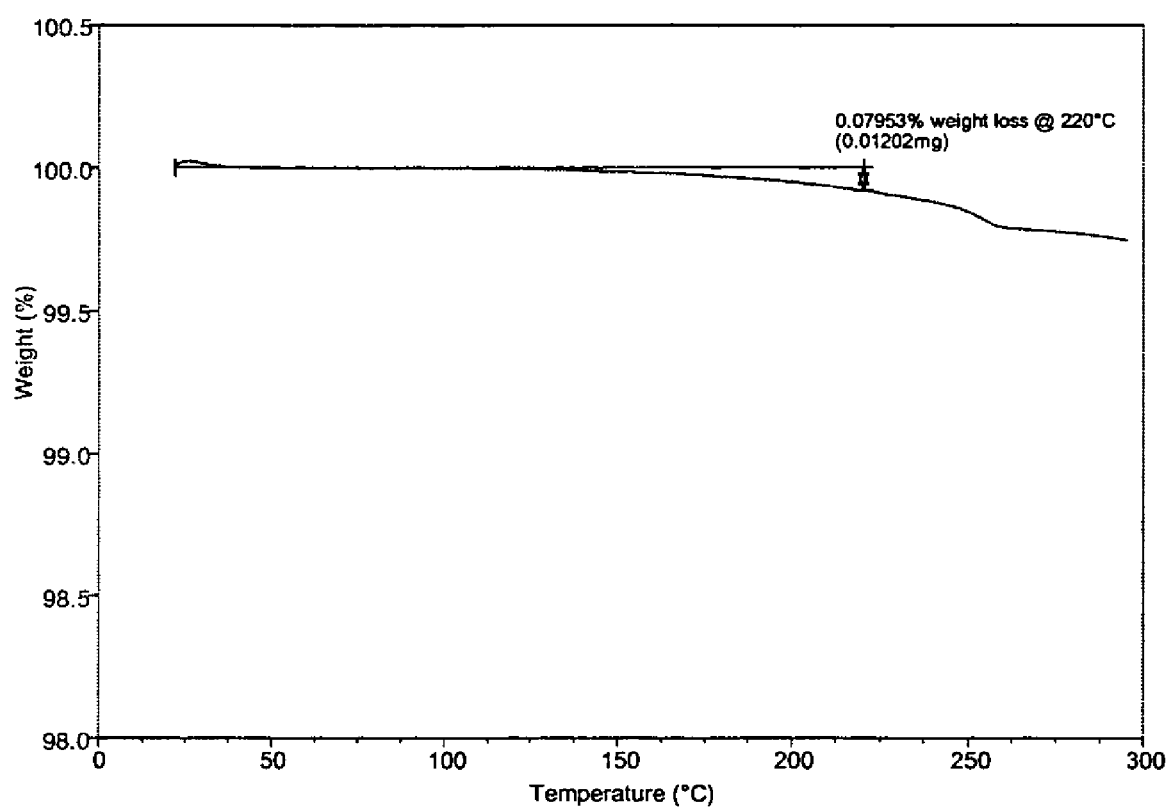

FIG. 12 shows thermogravimetric analysis thermogram of Form N-3 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 13:
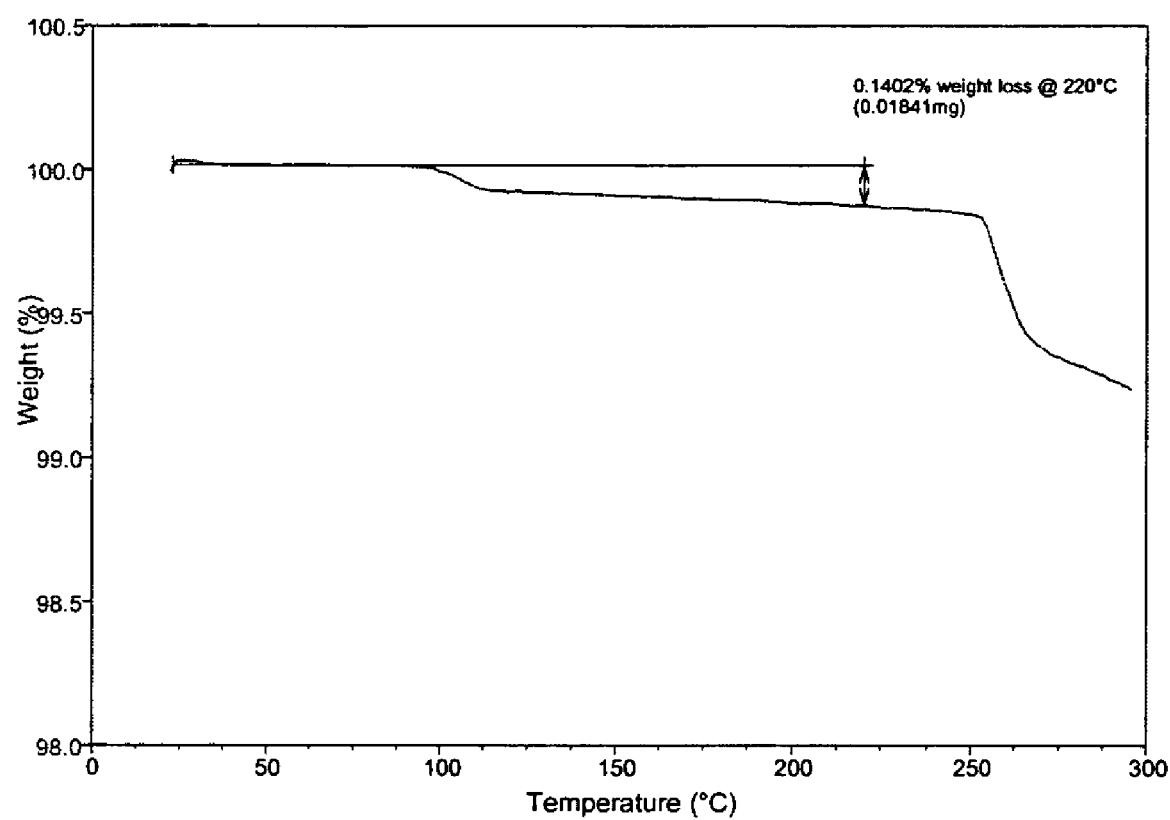

FIG. 13 shows thermogravimetric analysis thermogram of Form N-1 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 14:
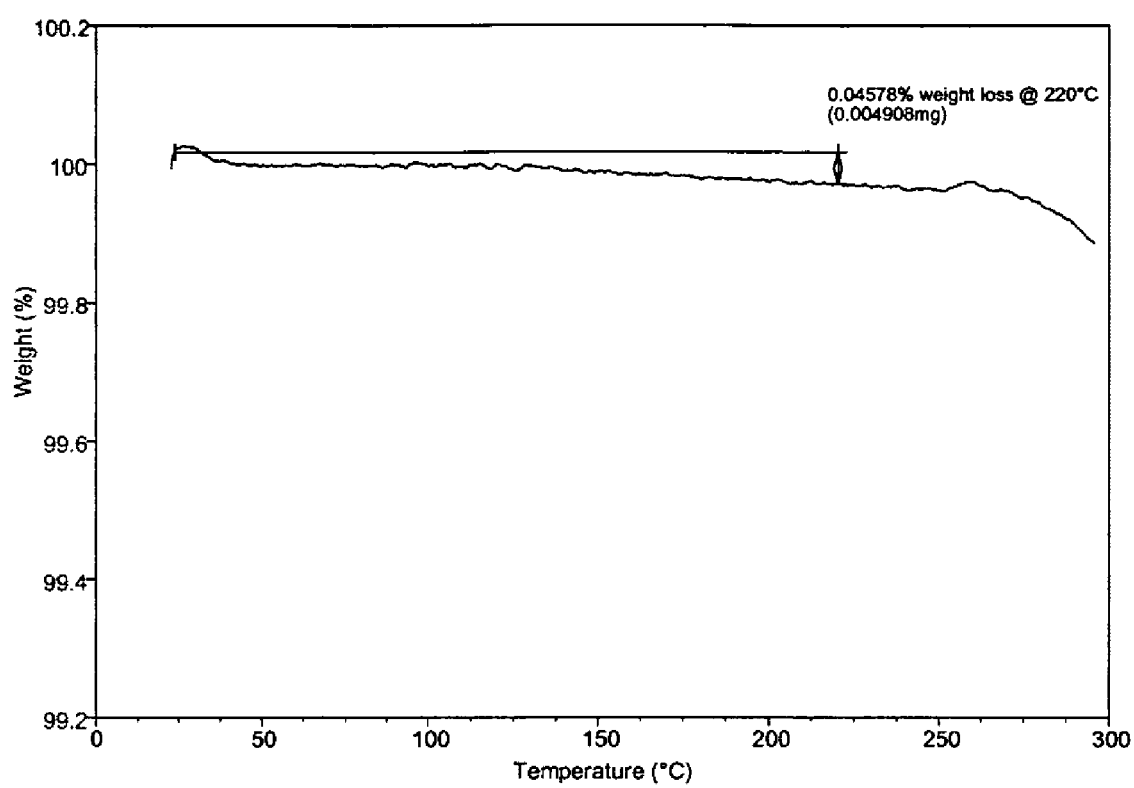

FIG. 14 shows thermogravimetric analysis thermogram of Form N-2 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 15:
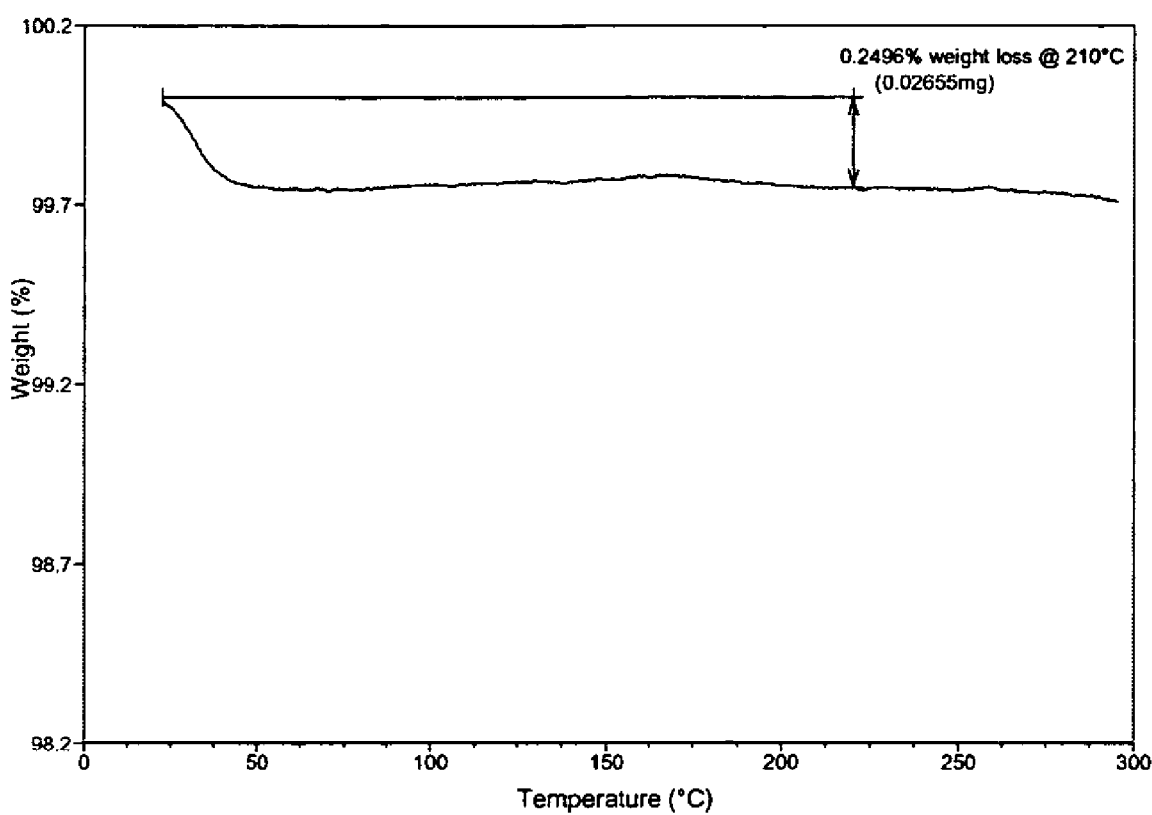

FIG. 15 shows thermogravimetric analysis thermogram of Phase P-1 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 16:
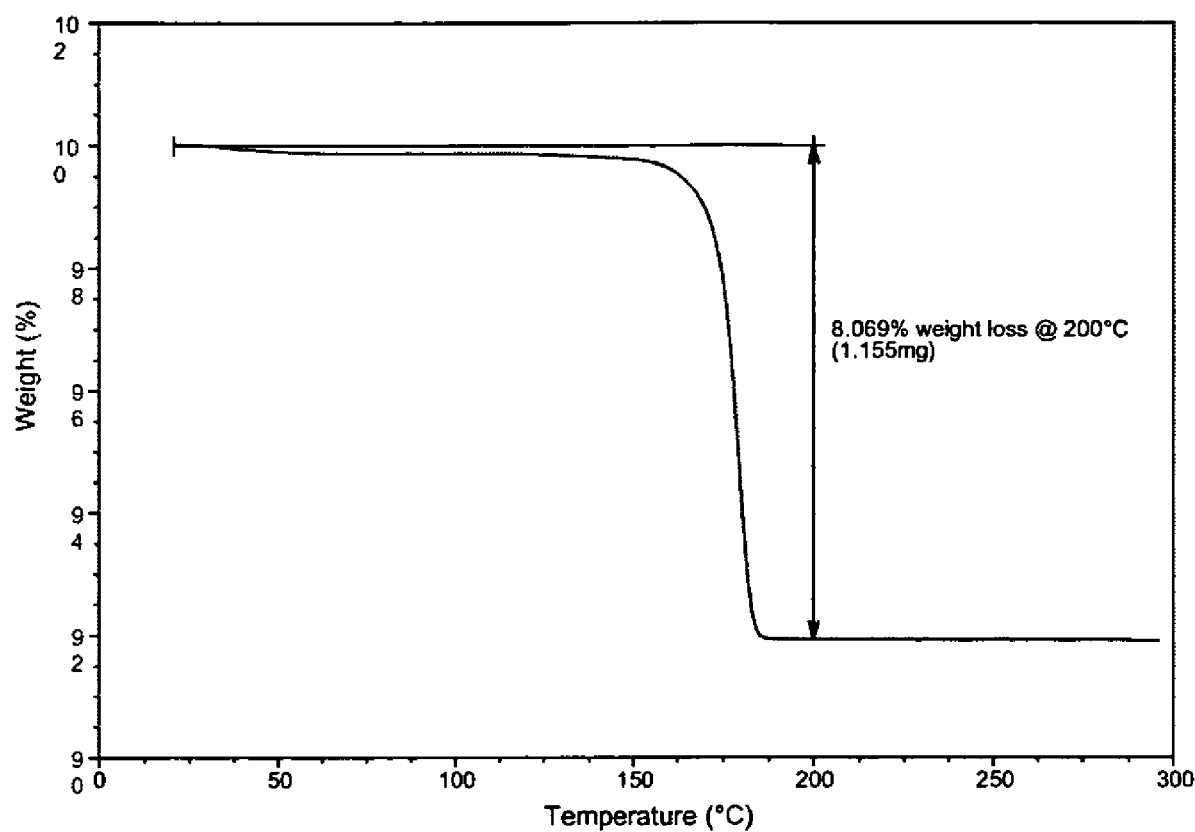

FIG. 16 shows thermogravimetric analysis thermogram of Form 0.5SBu-4 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Figure 17:
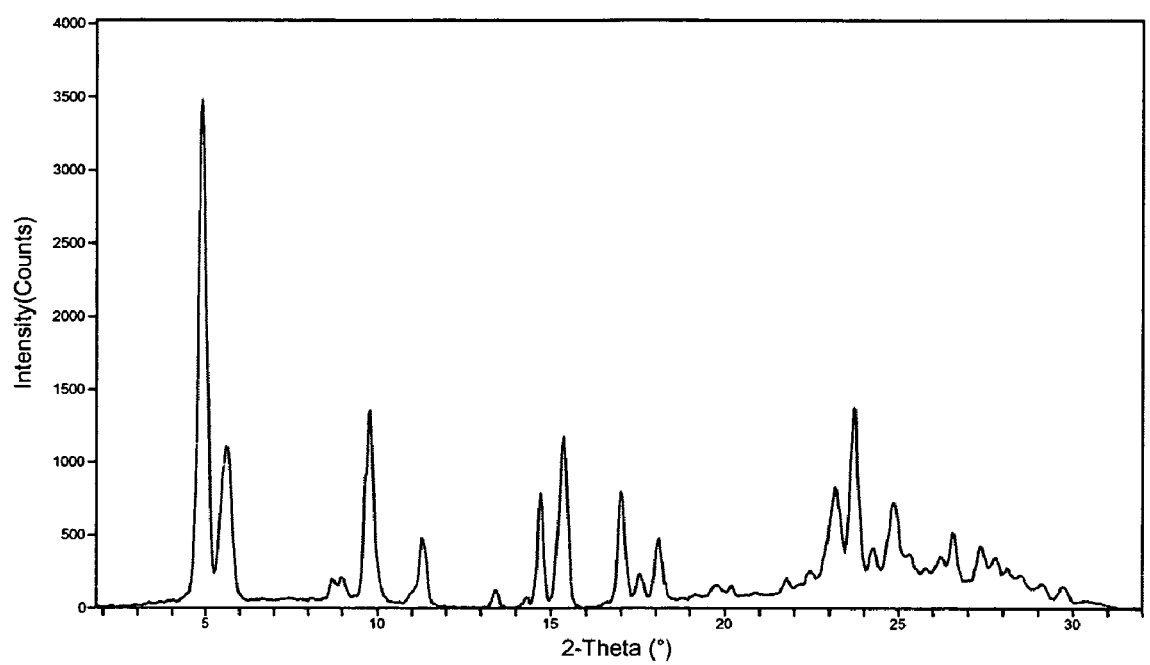

FIG. 17 shows observed (room temperature) powder X-ray diffraction pattern (CuKα λ=1.5418 Å) of Phase P-3 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

DETAILED DESCRIPTION OF THE INVENTION

The present invention provides, at least in part, crystalline forms of Compound (I) as a novel material, in particular in pharmaceutically acceptable form. The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, Compound (I) is in substantially pure form. The term "substantially pure", as used herein, means a compound having a purity greater than about 90% including greater than 90, 91, 92, 93, 94, 95, 96, 97, 98, and 99 weight %, and also including equal to about 100 weight % of Compound (I), based on the weight of the compound. The remaining material comprises other form(s) of the compound, and/or reaction impurities and/or processing impurities arising from its preparation. For example, a crystalline form of Compound (I) may be deemed substantially pure in that it has a purity greater than 90 weight %, as measured by means that are at this time known and generally accepted in the art, where the remaining less than 10 weight % of material comprises other form(s) of Compound (I) and/or reaction impurities and/or processing impurities.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate.

As used herein "amorphous" refers to a solid form of a molecule, atom, and/or ions that is not crystalline. An amorphous solid does not display a definitive X-ray diffraction pattern.

Compound (I) may be prepared using methods well known to the skilled artisan of organic synthesis, as well as methods taught in commonly assigned Application Publication No. 2003/0191115, U.S. Provisional Applications 60/613,754, 60/637,623, 60/613,943, and 60/613,982 and concurrently filed applications, the disclosures of which are hereby incorporated herein by reference, in their entireties.

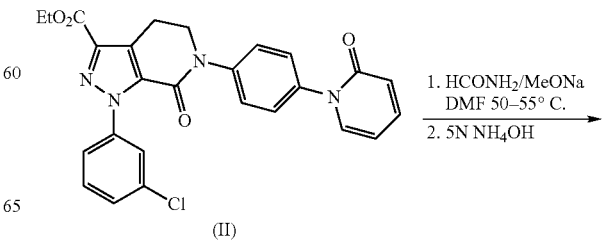

-continued

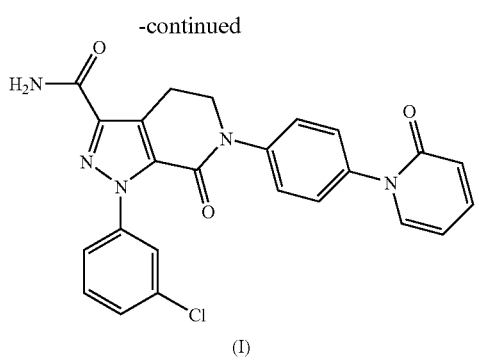

(I)

Compound (I) is formed from the ethyl ester (II) using formamide and sodium methoxide in DMF at 50° C. to 55° C. Ammonium hydroxide is slowly added at 50 to 55° C. The slurry is cooled to 20 to 25° over at least one hour and held at 20 to 25° C. for at least one hour. The slurry is then filtered and washed twice with water (WPUR) and once with acetone. The resulting product is then dried under vacuum at 50° C. with a nitrogen bleed to form P-1.

Samples of the crystalline forms may be provided with substantially pure phase homogeneity, indicating the presence of a dominant amount of a single polymorph and optionally minor amounts of one or more other polymorphs. The presence of more than one polymorph in a sample may be determined by techniques such as powder x-ray diffraction (XRPD) or solid state nuclear magnetic resonance spectroscopy (SSNMR). For example, the presence of extra peaks in the comparison of an experimentally measured XRPD pattern with a simulated XRPD pattern may indicate more than one polymorph in the sample. The simulated XRPD may be calculated from single crystal x-ray data. see Smith, D. K., "*A FORTRAN Program for Calculating X-Ray Powder Diffraction Patterns*," Lawrence Radiation Laboratory, Livermore, Calif., UCRL-7196, April 1963. Preferably, the crystalline form has substantially pure phase homogeneity as indicated by less than 10%, preferably less than 5%, and more preferably less than 2% of the total peak area in the experimentally measured XRPD pattern arising from the extra peaks that are absent from the simulated XRPD pattern. Most preferred is a crystalline form having substantially pure phase homogeneity with less than 1% of the total peak area in the experimentally measured XRPD pattern arising from the extra peaks that are absent from the simulated XRPD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind., 1999.

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility. Suitable solvents for preparing crystals include polar and nonpolar solvents.

In one method to prepare crystals, Compound (I) is suspended and/or stirred in a suitable solvent to afford a slurry, which may be heated to promote dissolution. The term "slurry", as used herein, means a saturated solution of Compound (I), which may also contain an additional amount of Compound (I) to afford a heterogeneous mixture of Compound (I) and a solvent at a given temperature. Suitable solvents in this regard include, for example, polar aprotic solvents, polar protic solvents, and nonpolar solvents, and mixtures of two or more of these.

Suitable polar aprotic solvents include, for example, acetone, methyl ethyl ketone (MEK), 1,3-dimethyl-3,4,5,6-tetrahydro-2(1H)-pyrimidinone (DMPU), 1,3-dimethyl-2-imidazolidinone (DMI), N-methylpyrrolidinone (NMP), N-methylacetamide, N-methylformamide, acetonitrile (ACN), dimethylsulfoxide (DMSO), propionitrile, ethyl formate, methyl acetate, ethyl acetate, isopropyl acetate (IpOAc), butyl acetate (BuOAc), t-butyl acetate, hexachloroacetone, dioxane, sulfolane, N,N-dimethylpropionamide, nitromethane, nitrobenzene and hexamethylphosphoramide.

Suitable polar protic solvents include, for example, alcohols and glycols, such as methanol, ethanol, 1-propanol, 2-propanol, isopropanol (IPA), 1-butanol (1-BuOH), 2-butanol (2-BuOH), i-butyl alcohol, t-butyl alcohol, 2-nitroethanol, 2-fluoroethanol, 2,2,2-trifluoroethanol, ethylene glycol, 2-methoxyethanol, 2-ethoxyethanol, diethylene glycol, 1-, 2-, or 3-pentanol, neo-pentyl alcohol, t-pentyl alcohol, diethylene glycol monomethyl ether, cyclohexanol, benzyl alcohol, phenol and glycerol.

Suitable nonpolar solvents include, for example, methyl tertiary butyl ether (MTBE), hexane and heptane.

Preferred solvents include, for example, acetone, ACN, DMSO, DMF, NMP, MEK, 2-BuOH, IPA, IpOAc, MTBE, and BuOAc.

Other solvents suitable for the preparation of slurries of Compound (I), in addition to those exemplified above, would be apparent to one skilled in the art, based on the present disclosure.

Seed crystals may be added to any crystallization mixture to promote crystallization. As will be clear to the skilled artisan, seeding is used as a means of controlling growth of a particular polymorph or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. Nyvlt, *Chemical Engineering Science*, 1971, 26, 369-377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e. change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, XRPD, or the like, to assure formation of the preferred crystalline form of the product. The resulting crystalline form is typically produced in an amount of greater than about 70 weight % isolated yield, but preferably greater than 90 weight % based on the weight of Compound (I) originally employed in the crystallization procedure. The product may be comilled or passed through a mesh screen to delump the product, if necessary.

Crystalline forms may be prepared directly from the reaction medium of the final process step for preparing Compound (I). This may be achieved, for example, by employing in the final process step a solvent or mixture of solvents from which Compound (I) may be crystallized. Alternatively, crystalline forms may be obtained by distillation or solvent addition techniques. Suitable solvents for this purpose include any of those solvents described herein, including protic polar solvents such as alcohols, and aprotic polar solvents such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like, by way of general guidance, the reaction solution may be distilled to about {fraction (1/10)} the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice as discussed above in connection with solvent exchange. Although the final concentration may vary depending on desired purity, recovery and the like, the final concentration of Compound (I) in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, solid state nuclear magnetic resonance (SSNMR) spectroscopy, X-ray powder diffraction (XRPD), differential scanning calorimetry (DSC), and/or thermogravimetric analysis (TGA).

Compound (I) may be present in the novel crystalline forms as the neat form, solvate and/or hydrate. A wide variety of solvents may be employed in the preparation of the solvates of Compound (I). Preferred solvents include, for example, polar solvents, including polar protic and polar aprotic solvents. In preferred form, the solvent employed in the preparation include, for example, DMF or acetone, preferably acetone. The ratio of Compound (I) to solvent in the solvates may vary and depends, for example, on the particular solvent selected and the methods for preparing the solvates.

Three neat crystalline forms, N-3 (also known as P-2), N-1 and N-2 (also known as P-4), a desolvated phase, P-1, and a hemi sec-BuOH solvate Form 0.5SBu-4 have been identified.

Figure 1:
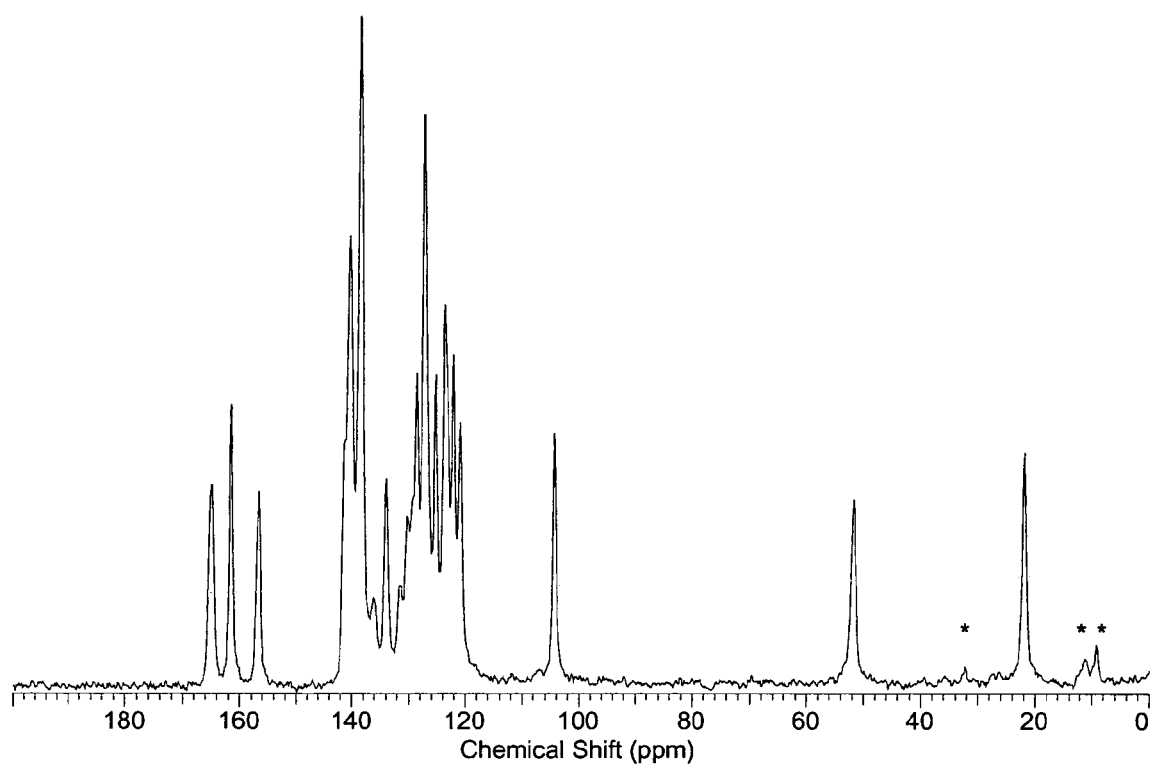
FIG. 1 shows C-13 CP-MAS SSNMR spectrum of Form N-3 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

Form N-3 is a neat, crystalline and nonhygroscopic form. In one aspect of the present invention, Form N-3 of Compound (I) may be characterized by C-13 SSNMR spectrum shown in FIG. 1.

Figure 2:
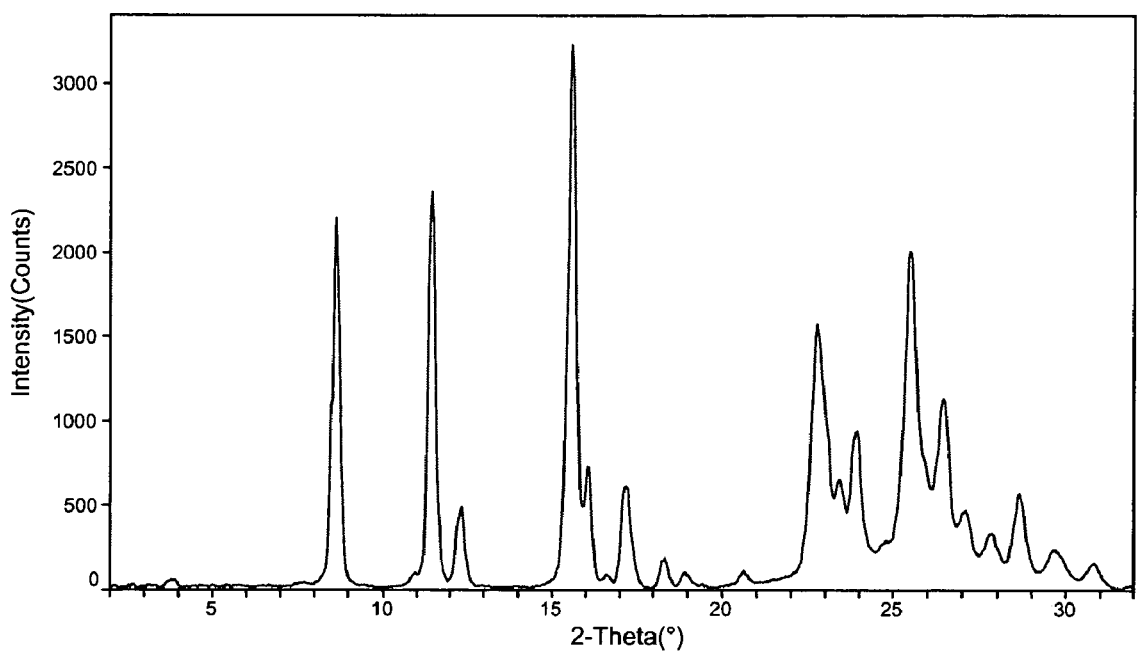
FIG. 2 shows the observed (room temperature) powder X-ray diffraction patterns (CuKα λ=1.5418 Å) of Form N-3 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide.

In a different aspect, Form N-3 may be characterized by a powder X-ray diffraction pattern substantially in accordance with that shown in FIG. 2.

In a different aspect, Form N-3 may be characterized by a powder X-ray diffraction pattern comprising the following 2θ values (CuKα λ=1.5418 Å): 8.6±0.2, 11.4±0.2, 12.3±0.2 and 15.6±0.2, at about 22° C.

In a different aspect, Form N-3 may be characterized by a differential scanning calorimetry thermogram (FIG. 7), having a peak onset at about 245-253° C.

SSNMR and XRPD indexing studies have proven that Form N-3 is a single phase. No significant weight loss was observed up to about 250° C. in TGA analysis. Form N-3 form has been shown to be physically stable by accelerated stability studies under the conditions of 40° C./75% RH/Open/4 Weeks and 50° C./Closed/4 Weeks. Form N-3 is non-hygroscopic as indicated by moisture sorption and desorption studies in which 0.4% moisture sorption was observed up to 95% RH at 25° C. and no hysteresis was observed. Form N-3 has the tendency to form small primary particles (<10 μm) of the shape of needles or rods. Form N-3 is thermodynamically more stable than polymorphs N-1 and N-2 at 25° C. to 60° C.

Form N-1 is a neat crystalline form crystallized from heptane/2-butanol at about 60° C. In one aspect of the present invention, Form N-1 of Compound (I) may be characterized by unit cell parameters substantially equal to the following:

| Cell dimensions: | a = 44.272(1) Å |
| | b = 14.3594(4) Å |
| | c = 20.9164(6) Å |
| | β = 109.36(1) |
| Space group | C2/c |
| Molecules/asymmetric unit | 3 | wherein the crystalline form is at about +22° C.

In a different aspect, Form N-1 may be characterized by fractional atomic coordinates substantially as listed in Table 3.

In a different aspect, Form N-1 may be characterized by fractional atomic coordinates substantially as listed in Table 3a.

Figure 3:
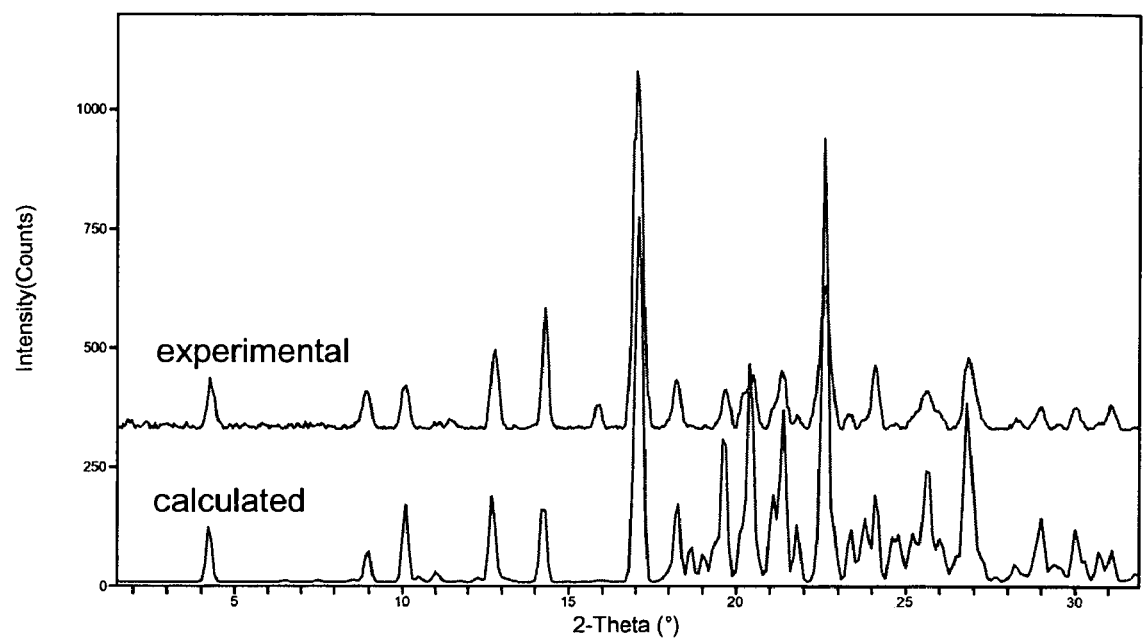
FIG. 3 shows calculated (22° C.) and experimental (room temperature) powder X-ray diffraction patterns (CuKα

In a different aspect, Form N-1 may be characterized by a powder X-ray diffraction pattern substantially in accordance with that shown in FIG. 3.

In a different aspect, Form N-1 may be characterized by a powder X-ray diffraction pattern comprising the following 2θ values (CuKα λ=1.5418 Å): 4.3±0.2, 10.1±0.2, 14.3±0.2 and 17.1±0.2, at about 22° C.

Form N-1 is physically unstable as indicated by the significant change in XRPD patterns of the stability samples stressed under the conditions of 40° C./75% RH/Open/4 Weeks and 50° C./Closed/4 Weeks. Form N-1 undergoes a solid-state transition at about 90° C. as evidenced by hot-stage microscopy studies and converts to Form N-2 at about 90° C. which is confirmed by single crystal XRPD studies. Thermal analysis by DSC (FIG. 8) and TGA show a small exotherm at about 113° C., which is attributed to the solid-state transition to Form N-2, followed by a melting endotherm at about 255 to about 259° C. similar to the melting range for Form N-2.

Form N-2 is a neat crystalline form and its single crystals can be obtained from a partial melt of Form N-1 or Form N-3 at about 250° C. The bulk powder of N-2 can be prepared by heating P-1 solid at about 230° C. In one aspect of the present invention, Form N-2 of Compound (I) may be characterized by unit cell parameters substantially equal to the following:

| Cell dimensions: | a = 26.004(1) Å |
| | b = 4.063(1) Å |
| | c = 22.653(1) Å |
| | β = 115.95(1) |
| Space group | Pc |
| Molecules/asymmetric unit | 2 | wherein the crystalline form is at about +22° C.

In a different aspect, Form N-2 may be characterized by fractional atomic coordinates substantially as listed in Table 4.

In a different aspect, Form N-2 may be characterized by a powder X-ray diffraction pattern substantially in accordance with that shown in FIG. 4.

In a different aspect, Form N-2 may be characterized by a powder X-ray diffraction pattern comprising the following 2θ values (CuKα λ=1.5418 Å): 8.8±0.2, 11.4±0.2, 13.9±0.2, 15.7±0.2 and 22.4±0.2, at about 22° C.

In a different aspect, Form N-2 may be characterized by a differential scanning calorimetry thermogram (FIG. 9), having a peak onset at about 254-258° C.

A stability study indicated that Form N-2 was physically stable and no significant physical changes were observed for the Form N-2 samples stored under the stressed conditions of 40° C./75% RH/Open for 5 Weeks and 50° C./Closed for 4 Weeks. A moisture sorption and desorption study indicated that Form N-2 is nonhygroscopic and no significant moisture adsorption (~1.2% moisture adsorption at 90% RH at 25° C.) was observed in this study. It has also been shown that N-2 is thermodynamically less stable than polymorph N-3 and converts to N-3 in slurry at 25 and 60° C.

P-1 is a desolvated phase obtained by drying the initial material (potential solvates) crystallized from the reaction mixture. P-1 has never been observed in slurry, and therefore there is no evidence to support assignment of P-1 as a single and neat phase that is crystallized directly from the reaction mixture. SSNMR studies suggest that P-1 may not be a single phase material. P-1 converts to Form N-3 in solvents (e.g., acetone) and to a number of potential solvates in slurry in different solvent systems. P-1 can also convert to Form N-2 upon heating at 230° C. in solid state. P-1 is physically unstable as indicated by accelerated stability studies in which significant physical change has been observed by XRPD assay (FIG. 5) for the samples stressed for 3 weeks under the condition of 40° C./75% RH/Open. DSC thermal analysis (FIG. 10) shows that P-1 melts at ~223° C., recrystallizes to Form N-2 at ~225° C., which subsequently melts between 255-259° C. A moisture sorption and desorption study of the P-1 material showed ~16% weight gain on adsorption to 90% RH, indicating P-1 is hygroscopic.

In one aspect, P-1 may be characterized by a powder X-ray diffraction pattern substantially in accordance with that shown in FIG. 5.

In a different aspect, P-1 may be characterized by a powder X-ray diffraction pattern comprising the following 2θ values (CuKα λ=1.5418 Å):5.5±0.2, 11.1±0.2, 15.4±0.2, 16.8±0.2, at about 22° C.

Scheme 1 illustrates the conversion of different crystalline forms of Compound (I) under certain conditions.

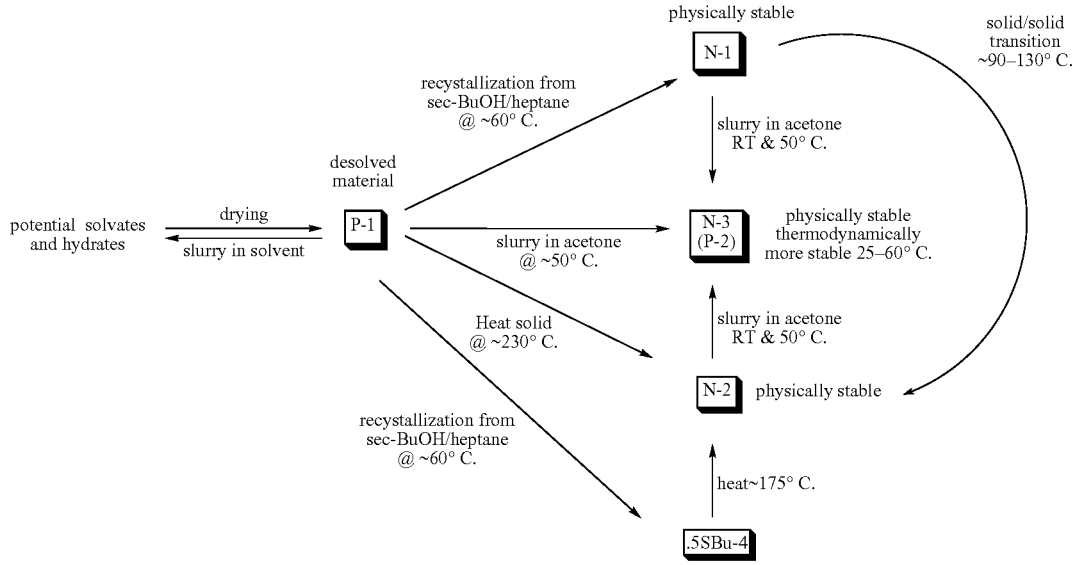

Scheme 1

P-1 converts to Form N-3, the thermodynamically more stable neat form readily in slurry in different solvents (e.g., acetone, ACN, DMSO/MTBE) at about 50° C. A Good Laboratory Practice batch (~550 g) of Form N-3 has been manufactured successfully by converting P-1 material using a slurry method in acetone at about 50° C. Acetone slurries of Form P-1 spiked at about 50° C. with 1% water still yield Form N-3, but the slurries spiked with 5% and 10% water result in P-3 (solvated) material. P-1 also converts to Form N-2, a physically stable neat form upon heating at about 230° C. in solid state. Form N-2, in turn, converts to Form N-3 readily in slurry in acetone at RT or about 50° C. The hemi sec BuOH solvate, form 0.5SBU-4, converts to form N-2 upon heating. Recrystallization of P-1 at dilute concentration in sec-butanol/heptane (1:2) at about 60° C. provides Form N-1, an unstable neat form which also converts to N-3 readily in slurry in acetone. Form N-1 also undergoes a solid state transition to Form N-2 upon heating at about 90 to 130° C. In addition, P-1 converts to potential solvate/hydrate forms by slurrying in different solvent systems, e.g., MeOH/EtOAc, DMF/$H_2O$, DMSO/$H_2O$, NMP/$H_2O$ at room temperature or at about 50° C. The fact that P-1, Form N-1 and Form N-2 all convert to Form N-3 in slurry confirms that Form N-3 is the thermodynamically more stable polymorph at room temperature to 60° C. and a preferred form.

In a different aspect, Form 0.5SBu-4 of Compound (I) may be characterized by unit cell parameters substantially equal to the following:

| Cell dimensions: | a = 10.688(1) Å |
| --- | --- |
|  | b = 15.006(2) Å |
|  | c = 16.041(2) Å |
|  | α = 85.51(1) |
|  | β = 83.15(1) |
|  | γ = 74.13(1) |
| Space group | P-1 |
| Molecules/asymmetric unit | 2 | wherein the crystalline form is at about +22° C.

In a different aspect, Form 0.5SBu-4 may be characterized by fractional atomic coordinates substantially as listed in Table 5.

In a different aspect, Form 0.5SBu-4 may be characterized by fractional atomic coordinates substantially as listed in Table 5a.

In a different aspect, Form 0.5SBu-4 may be characterized by a powder X-ray diffraction pattern substantially in accordance with that shown in FIG. 6.

In a different aspect, Form 0.5SBu-4 may be characterized by a powder X-ray diffraction pattern comprising the following 2θ values (CuKα λ-=1.5418 Å): 6.1±0.2, 8.1±0.2, 12.9±0.2, 13.4±0.2 and 18.5.±0.2, at about 22° C.

In a different aspect, Form 0.5SBu-4 may be characterized by a differential scanning calorimetry thermogram (FIG. 11) having a peak at about 150-200° C.

In a different aspect, Form 0.5SBu-4 may be characterized by a thermal gravimetric analysis curve (FIG. 16) having a weight loss of about 7.5% at about 200° C.

P-3 represents a family of solvated phases with similar powder patterns and therefore similar crystal structures. P-3 crystallized from various solvents (e.g. ETOH, MEOH, ETOAC) convert to P-1 upon isolation and drying at elevated temperatures. In such cases, P-3 has only been observed in the slurry. P-3 crystallized from other solvents (e.g DMF/water, NMP/water) remains P-3 after isolation and drying.

In one aspect, P-3 may be characterized by a powder X-ray diffraction pattern substantially in accordance with that shown in FIG. 17.

In a different aspect, P-3 may be characterized by a powder X-ray diffraction pattern comprising the following 2θ values (CuKα λ=1.5418 Å): 4.9±0.8, 5.6±0.8, 9.8±0.8, 15.4±0.8, 17.0±0.8 and 23±0.8, at about 22° C.

The crystalline forms of Compound (I) described herein may be formulated into pharmaceutical compositions and/or employed in therapeutic and/or prophylactic methods. These methods include, but are not limited to, the administration of the crystalline compound (I), alone or in combination with one or more other pharmaceutically active agents, including agents that may be useful in the treatment of the disorders mentioned herein.

"Therapeutically effective amount" is intended to include an amount of the crystalline forms of Compound (I) that is effective when administered alone or in combination to inhibit factor Xa. If Compound (I) is used in combination with another medication, the combination of compounds described herein may result in a synergistic combination. Synergy, as described for example by Chou and Talalay, *Adv. Enzyme Regul.* 1984, 22, 27-55, occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antithrombotic effect, or some other beneficial effect of the combination compared with the individual components.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

The crystalline forms of Compound (I) and pharmaceutical compositions thereof may be useful in inhibiting Factor Xa. Accordingly, the present invention provides methods for the treatment and/or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The methods preferably comprise administering to a patient a pharmaceutically effective amount of the novel crystals of the present invention, preferably in combination with one or more pharmaceutically acceptable carriers and/or excipients. The relative proportions of active ingredient and carrier and/or excipient may be determined, for example, by the solubility and chemical nature of the materials, chosen route of administration and standard pharmaceutical practice.

The crystalline forms of Compound (I) may be administered to a patient in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They may be administered alone, but generally will be administered with a pharmaceutical carrier selected on the basis of the chosen route of administration and standard pharmaceutical practice.

The dosage regimen for the crystalline forms of Compound (I) will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. Several unit dosage forms may be administered at about the same time. The dosage of the crystalline form of Compound (I) that will be most suitable for prophylaxis or treatment may vary with the form of administration, the particular crystalline form of the compound chosen and the physiological characteristics of the particular patient under treatment. Broadly, small dosages may be used initially and, if necessary, increased by small increments until the desired effect under the circumstances is reached.

By way of general guidance, in the adult, suitable doses may range from about 0.001 to about 1000 mg/Kg body weight, and all combinations and subcombinations of ranges and specific doses therein. Preferred doses may be from about 0.01 to about 100 mg/kg body weight per day by inhalation, preferably 0.1 to 70, more preferably 0.5 to 20 mg/Kg body weight per day by oral administration, and from about 0.01 to about 50, preferably 0.01 to 10 mg/Kg body weight per day by intravenous administration. In each particular case, the doses may be determined in accordance with the factors distinctive to the subject to be treated, such as age, weight, general state of health and other characteristics which can influence the efficacy of the medicinal product. The crystalline forms of Compound (I) may be administered in a single daily dose, or the total daily dosage may be administered in divided doses of two, three, or four times daily.

For oral administration in solid form such as a tablet or capsule, the crystalline forms of Compound (I) can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms may contain a number of additional ingredients referred to herein as "excipients". These excipients include among others diluents, binders, lubricants, glidants and disintegrants. Coloring agents may also be incorporated. "Diluents", as used herein, are agents which impart bulk to the formulation to make a tablet a practical size for compression. Examples of diluents are lactose and cellulose. "Binders", as used herein, are agents used to impart cohesive qualities to the powered material to help ensure the tablet will remain intact after compression, as well as improving the free-flowing qualities of the powder. Examples of typical binders are lactose, starch and various sugars. "Lubricants", as used herein, have several functions including preventing the adhesion of the tablets to the compression equipment and improving the flow of the granulation prior to compression or encapsulation. Lubricants are in most cases hydrophobic materials. Excessive use of lubricants is undesired, however, as it may result in a formulation with reduced disintegration and/or delayed dissolution of the drug substance. "Glidants", as used herein, refer to substances which may improve the flow characteristics of the granulation material. Examples of glidants include talc and colloidal silicon dioxide. "Disintegrants", as used herein, are substances or a mixture of substances added to a formulation to facilitate the breakup or disintegration of the solid dosage form after administration. Materials that may serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

The disintegrant preferably used in the present invention is selected from the group comprising modified starches, croscarmallose sodium, carboxymethylcellulose calcium and crospovidone. A more preferred disintegrant in the present invention is a modified starch such as sodium starch glycolate.

Preferred carriers include capsules or compressed tablets which contain the solid pharmaceutical dosage forms described herein. Preferred capsule or compressed tablet forms generally comprise a therapeutically effective amount of the crystalline forms of Compound (I) and one or more disintegrants in an amount greater than about 10% by weight relative to the total weight of the contents of the capsule or the total weight of the tablet.

Preferred capsule formulations may contain the crystalline forms of Compound (I) in an amount from about 5 to about 1000 mg per capsule. Preferred compressed tablet formulations contain the crystalline forms of Compound (I) in an amount from about 5 mg to about 800 mg per tablet. More preferred formulations contain about 50 to about 200 mg per capsule or compressed tablet. Preferably, the capsule or compressed tablet pharmaceutical dosage form comprises a therapeutically effective amount of Form N-1 of Compound (I); a surfactant; a disintegrant; a binder; a lubricant; and optionally additional pharmaceutically acceptable excipients such as diluents, glidants and the like; wherein the disintegrant is selected from modified starches; croscarmallose sodium, carboxymethylcellulose calcium and crospovidone.

For oral administration in liquid form, the crystalline forms of Compound (I) can be combined with any oral, non-toxic pharmaceutically acceptable inert carrier such as ethanol, glycerol, water and the like. The liquid composition may contain a sweetening agent which to make the compositions more palatable. The sweetening agent can be selected from a sugar such as sucrose, mannitol, sorbitol, xylitol, lactose, etc. or a sugar substitute such as cyclamate, saccharin, aspartame, etc. If sugar substitutes are selected as the sweetening agent the amount employed in the compositions of the invention will be substantially less than if sugars are employed. Taking this into account, the amount of sweetening agent may range from about 0.1 to about 50% by weight, and all combinations and subcombinations of ranges and specific amounts therein. Preferred amounts range from about 0.5 to about 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen, and all combinations and subcombinations of ranges and specific particle sizes therein.

Sterile injectable solutions may be prepared by incorporating the crystalline forms of Compound (I) in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof.

As would be apparent to a person of ordinary skill in the art, once armed with the teachings of the present disclosure, when dissolved, Compound (I) loses its crystalline structure, and is therefore considered to be a solution of Compound (I). All forms of the present invention, however, may be used for the preparation of liquid formulations in which Compound (I) may be, for example, dissolved or suspended. In addition, the crystalline forms of Compound (I) may be incorporated into solid formulations.

The liquid compositions may also contain other components routinely utilized in formulating pharmaceutical compositions. One example of such components is lecithin. Its use in compositions of the invention as an emulsifying agent in the range of from 0.05 to 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

The crystalline forms of Compound (I) may also be coupled with soluble polymers as targetable drug carriers. Such polymers can include polyvinylpyrrolidine pyran copolymer, polyhydroxypropylmethacrylamide-phenol, polyhydroxyethyl-aspartamidephenol or polyethylene oxide-polylysine substituted with palmitoyl residues. Furthermore, the crystalline Compound (I) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Gelatin capsules of the crystalline forms of Compound (I) may contain the crystalline Compound (I) and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the crystalline Compound (I) in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chloride, methyl- or propyl-paraben and chlorobutanol.

Suitable pharmaceutical carriers are described in Remington's Pharmaceutical Sciences, Mack Publishing Co., the disclosures of which are hereby incorporated herein by reference, in their entireties. Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient (i.e., Factor Xa inhibitor), 150 mg of lactose, 50 mg of cellulose, and 6 mg magnesium stearate.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Nasal Spray

An aqueous solution is prepared such that each 1 mL contains 10 mg of active ingredient, 1.8 mg methylparaben, 0.2 mg propylparaben and 10 mg methylcellulose. The solution is dispensed into 1 mL vials.

Lung Inhaler

A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

The preferred crystalline form of Compound (I) may serve as component (a) of this invention and can independently be in any dosage form, such as those described above, and can also be administered in various combinations, as described above. In the following description component (b) is to be understood to represent one or more agents as described herein suitable for combination therapy.

Thus, the crystalline forms of Compound (I) may be used alone or in combination with other diagnostic, anticoagulant, antiplatelet, fibrinolytic, antithrombotic, and/or profibrinolytic agents. For example, adjunctive administration of Factor Xa inhibitors with standard heparin, low molecular weight heparin, direct thrombin inhibitors (i.e. hirudin), aspirin, fibrinogen receptor antagonists, streptokinase, urokinase and/or tissue plasminogen activator may result in improved antithrombotic or thrombolytic efficacy or efficiency. The crystals described herein may be administered to treat thrombotic complications in a variety of animals, such as primates, including humans, sheep, horses, cattle, pigs, dogs, rats and mice. Inhibition of Factor Xa may be useful not only in the anticoagulant therapy of individuals having thrombotic conditions, but also when inhibition of blood coagulation may be required, such as to prevent coagulation of stored whole blood and to prevent coagulation in other biological samples for testing or storage. Thus, any Factor Xa inhibitor, including the crystalline forms of Compound (I) as described herein, can be added to or contacted with any medium containing or suspected of containing Factor Xa and in which it may be desired to inhibit blood coagulation.

The crystalline forms of Compound (I) may be used in combination with any antihypertensive agent or cholesterol or lipid regulating agent, or concurrently in the treatment of restenosis, atherosclerosis or high blood pressure. Some examples of agents that may be useful in combination with a novel form of Compound (I) according to the present invention in the treatment of high blood pressure include, for example, compounds of the following classes: beta-blockers, ACE inhibitors, calcium channel antagonists and alpha-receptor antagonists. Some examples of agents that may be useful in combination with a compound according to the invention in the treatment of elevated cholesterol levels or disregulated lipid levels include compounds known to be HMGCoA reductase inhibitors, or compounds of the fibrate class.

Accordingly, components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the reverse order. If component (b) contains more that one agent, these agents may be administered together or in any order. When not administered at the same time, preferably the administration of component (a) and (b) occurs less than about one hour apart. Preferably, the route of administration of component (a) and (b) is oral. Although it may be preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

Pharmaceutical kits which may be useful for the treatment of various disorders, and which comprise a therapeutically effective amount of a pharmaceutical composition comprising a novel form of Compound (I) in one or more sterile containers, are also within the ambit of the present invention. The kits may further comprise conventional pharmaceutical kit components which will be readily apparent to those skilled in the art, once armed with the present disclosure. Sterilization of the container may be carried out using conventional sterilization methodology well known to those skilled in the art.

The present invention is further described in the following examples. All of the examples are actual examples. These examples are not to be construed as limiting the scope of the appended claims.

EXAMPLES

Example 1

Preparation of P-1 from ethyl 1-(3-chlorophenyl)-7-oxo-6-(4-(2-oxopyridin-1(2H)-yl)phenyl)-4,5,6,7-tetrahydro-1H-pyrazolo[3,4-c]pyridine-3-carboxylate 0.690 Kg of ethyl 1-(3-chlorophenyl)-7-oxo-6-(4-(2-oxopyridin-1(2H)-yl)phenyl)-4,5,6,7-tetrahydro-1H-pyrazolo[3,4-c]pyridine-3-carboxylate was charged to a 20 L reactor at room temperature. 6.514 Kg of DMF and 1.565 Kg of formamide were charged to the 20 L reactor at room temperature. The batch was then heated to 50 to 55° C. and held at 50 to 55° C. for at least 10 minutes. 0.320 Kg of sodium methoxide 25% in methanol was then added while keeping the batch temperature at 50 to 55° C. After the sodim methoxide addition was completed, the batch was kept at 50 to 55° C. for at least 15 minutes. An in process control sample was taken to confirm the completion of the reaction. After the reaction was completed, 10% ammonium hydroxide was charged over at least one hour while keeping the batch at 50 to 55° C. The batch was then cooled to 20 to 25° C. over at least one hour and held at 20 to 25° C. for at least one hour. The slurry was then filtered and washed with 6.90 Kg of Water USP Bulk followed by a second wash of 6.90 Kg of Water USP Bulk. Finally, the cake was washed with 5.458 Kg of acetone and the cake suctioned for at least one hour. The wet solids were then dried under vacuum at 50° C. with a nitrogen bleed until a LOD of <2.0% is obtained.

Example 2

Preparation of Form N-1

To a one liter Erlemneyer flask, added 2.2 g of Example 1 and then added 250 mL sec-butanol. The mixture was heated to dissolve (~80° C.) and then filtered through a 600 mL coarse fritted funnel. 1000 mL sec-butanol was added and heated to dissolve any film on flask walls. 530 mL n-heptane was added portionwise over 15 minutes. The solution was seeded with Form N-1 from an earlier batch. It was aged for 24 hours, unstirred, on a hot plate between 40 and 50° C., then cooled gradually and aged at 20-25° C. for at least 24 hours.

Example 3

Preparation of Form N-2

635.2 mg of Example 1 was weighed out into a crucible. The crucible was placed in a furnace at 230° C., held at 230° C. for 2 hours or until no P-1 form was observed via XRPD and DSC. Form N-2 was then cooled to room temperature. 624.7 mg of N-2 form was collected.

Example 4

Preparation of Form N-3

0.615 Kg of Example 1 was charged to a 20 L reactor at room temperature. 9.730 Kg of acetone was then charged to the 20 L reactor at room temperature. The slurry was heated to 50 to 55° C. Once the batch reached 50 to 55° C., 10.0 grams of Form N-3 (from an earlier batch) in 150.0 grams of acetone were charged to the reactor. The reactor was monitored by Raman to observe the form conversion of P-1 to Form N-3. The batch was stirred between 50 and 55° C. until conversion was completed and verified via XRPD. The batch was then cooled to 20 to 25° C. over at least one hour and held at 20 to 25° C. for at least one hour. The slurry was then filtered and washed with 6.50 Kg of acetone and the cake suctioned for at least one hour. The wet solids were dried under vacuum at 50° C. with a nitrogen bleed until a loss on drying of <0.5% was obtained.

Example 5

Preparation of Form 0.5SBu4

Upon prolonged standing, crystals of Form 0.5SBu-4 crystallized from the mother liquors of N-1. The approximate solvent composition of the mother liquors was 30% n-heptane, 70% sec-butanol.

All solid-state C-13 NMR (SSNMR) measurements were made with a Bruker DSX-400, 400 MHz NMR spectrometer. High resolution spectra were obtained using high-power proton decoupling and the TPPM pulse sequence and ramp amplitude cross-polarization (RAMP-CP) with magic-angle spinning (MAS) at approximately 12 kHz (A. E. Bennett et al, *J. Chem. Phys.*, 1995, 103, 6951),(G. Metz, X. Wu and S. O. Smith, *J. Magn. Reson. A,*. 1994, 110, 219-227). Approximately 70 mg of sample, packed into a canister-design zirconia rotor was used for each experiment. Chemical shifts ($\delta$) were referenced to external adamantane with the high frequency resonance being set to 38.56 ppm (W. L. Earl and D. L. VanderHart, *J. Magn. Reson.*, 1982, 48, 35-54).

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

X-ray powder diffraction (PXRD) data were obtained using a Bruker C2 GADDS (General Area Detector Diffraction System). The radiation was Cu K$\alpha$ (40 KV, 50 mA). The sample-detector distance was 15 cm. Powder samples were placed in sealed glass capillaries of 1 mm or less in diameter; the capillary was rotated during data collection. Data were collected for $3 \leq 2\theta \leq 35°$ with a sample exposure time of at least 2000 seconds. The resulting two-dimensional diffraction arcs were integrated to create a traditional 1-dimensional PXRD pattern with a step size of 0.02 degrees $2\theta$ in the range of 3 to 35 degrees $2\theta$. Altherantively, about 200 mg were pack by the backloading method into a Philips powder X-ray diffraction (PXRD) sample holder. The sample was tranferred to a Philips MPD unit (45 KV, 40 mA, Cu K$\alpha_1$). Data were collected at room temperature in the 2 to 32 2-theta rage (continuous scanning mode, scanning rate 0.03 degrees/sec., auto divergence and anti scatter slits, receiving slit: 0.2 mm, sample spinner: ON).

Single crystal X-ray data were collected on a Bruker-Nonius CAD4 serial diffractometer (Bruker Axs, Inc., Madison Wis.). Unit cell parameters were obtained through least-squares analysis of the experimental diffractometer settings of 25 high-angle reflections. Intensities were measured using Cu K$\alpha$ radiation ($\lambda$=1.5418 Å) at a constant temperature with the $\theta$-2$\theta$ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu K$\alpha$ radiation ($\lambda$=1.5418 Å). Indexing and processing of the measured intensity data were carried out with the HKL2000 software package in the Collect program suite R.

Hooft, Nonius B. V. (1998). When indicated, crystals were cooled in the cold stream of an Oxford cryogenic system during data collection.

The structures were solved by direct methods and refined on the basis of observed reflections using either the SDP software package SDP, Structure Determination Package, Enraf-Nonius, Bohemia, N.Y.) with minor local modifications or the crystallographic package, MAXUS (maXus solution and refinement software suit: S. Mackay, C. J. Gilmore, C. Edwards, M. Tremayne, N. Stewart, and K. Shankland. maXus is a computer program for the solution and refinement of crystal structures from diffraction data.

The derived atomic parameters (coordinates and temperature factors) were refined through full matrix least-squares. The function minimized in the refinements was $\Sigma_w(|F_o|-|F_c|)^2$. R is defined as $\Sigma||F|-|F||/\Sigma|F_o|$ while $R^w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogen atoms were introduced in idealized positions with isotropic temperature factors, but no hydrogen parameters were varied.

Differential scanning calorimetry (DSC) experiments were performed in a TA Instruments™ model Q1000. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Thermal gravimetric analysis (TGA) experiments were performed in a TA Instruments™ model Q500. The sample (about 10-30 mg) was placed in a platinum pan previously tared. The weight of the sample was measured accurately and recorded to a thousand of a milligram by the instrument The furnace was purged with nitrogen gas at 100 mL/min. Data were collected between room temperature and 300° C. at 10° C./min heating rate.

Various crystalline forms of Compound (I) and its solvates were prepared and are tabulated in Table 1. The unit cell data and other properties for these examples are tabulated in Tables 2a and 2b. The unit cell parameters were obtained from single crystal X-ray crystallographic analysis. A detailed account of unit cells can be found in Chapter 3 of Stout & Jensen, "X-Ray Structure Determination: A Practical Guide", (MacMillian, 1968).

TABLE 1

| Form | Description |
| --- | --- |
| N-3 | Neat crystal |
| N-1 | Neat crystal |
| N-2 | Neat crystal |
| P-1 | desolvated phase |
| .5SBu-4 | hemi sec-BuOH solvate crystal |

TABLE 2a

Unit Cell Parameters

| Form | T (° C.) | a(Å) | b(Å) | c(Å) | α° | β° | γ° |
| --- | --- | --- | --- | --- | --- | --- | --- |
| N-1 | +22 | 44.272(1) | 14.3594(4) | 20.9164(6) | | 109.36(1) | |
| N-1 | −50 | 44.041(5) | 14.280(8) | 20.794(2) | | 109.07(1) | |
| N-2 | +22 | 26.004(1) | 4.063(1) | 22.653(1) | | 115.95(1) | |
| .5SBu-4 | −50 | 10.665(1) | 14.923(2) | 15.909(2) | 85.85(1) | 83.00(1) | 74.90(1) |
| .5SBu-4 | +22 | 10.688(1) | 15.006(2) | 16.041(2) | 85.51(1) | 83.15(1) | 74.13(1) |

TABLE 2b

Unit Cell Parameters (continued)

| Form | V(Å³) | Z' | SG | R | Solvent Sites for Z' |
| --- | --- | --- | --- | --- | --- |
| N-1 | 12545.2(6) | 3 | C2/c | .047 | None |
| N-1 | 12360(10) | 3 | C2/c | .065 | None |
| N-2 | 2152.1(5) | 2 | Pc | .050 | None |
| .5SBu-4 | 2424.3(6) | 2 | P-1 | .07 | .5 sec-BuOH |

Notes for Tables:
T is the temperature for the crystallographic data.
Z' is the number of molecules of Compound (I) in each asymmetric unit
SG is the crystallographic space group.
R is the R-factor (measure of the quality of the refinement).

The fractional atomic coordinates for the various crystalline forms are tabulated in Tables 3 to 5a.

TABLE 3

Positional Parameters and Isotropic Equivalent Temperature Factor Form N-1 at room temperature

| Atom | x | y | z | B (iso) |
| --- | --- | --- | --- | --- |
| CL1 | 0.0854 | 0.3279 | 0.5025 | 6.6 |
| O8 | 0.1369 | 0.2940 | 0.3265 | 5.7 |
| O26 | 0.3055 | 0.4347 | 0.3733 | 7.6 |
| N1 | 0.0700 | 0.3407 | 0.2490 | 4.2 |
| N2 | 0.0441 | 0.3635 | 0.1945 | 4.3 |
| N7 | 0.1526 | 0.4022 | 0.2632 | 4.3 |
| O17 | 0.0393 | 0.5210 | 0.0633 | 6.2 |
| N18 | 0.0054 | 0.4037 | 0.0646 | 5.1 |
| N25 | 0.2810 | 0.3263 | 0.4189 | 4.3 |
| C3 | 0.0555 | 0.4160 | 0.1548 | 4.0 |
| C4 | 0.0885 | 0.4286 | 0.1832 | 4.1 |
| C5 | 0.1135 | 0.4767 | 0.1612 | 4.8 |
| C6 | 0.1436 | 0.4891 | 0.2229 | 5.0 |
| C8 | 0.1305 | 0.3550 | 0.2834 | 4.2 |
| C9 | 0.0973 | 0.3793 | 0.2427 | 4.0 |
| C10 | 0.0646 | 0.2943 | 0.3043 | 3.9 |
| C11 | 0.0786 | 0.3264 | 0.3695 | 4.2 |
| C12 | 0.0701 | 0.2844 | 0.4205 | 4.5 |
| C13 | 0.0486 | 0.2119 | 0.4083 | 4.9 |
| C14 | 0.0349 | 0.1799 | 0.3424 | 5.2 |
| C15 | 0.0426 | 0.2211 | 0.2900 | 4.9 |
| C16 | 0.0328 | 0.4513 | 0.0900 | 4.4 |
| C19 | 0.1859 | 0.3851 | 0.2987 | 4.0 |
| C20 | 0.1979 | 0.2956 | 0.3002 | 4.5 |

TABLE 3-continued

Positional Parameters and Isotropic Equivalent Temperature Factor Form N-1 at room temperature

| Atom | x | y | z | B (iso) |
|---|---|---|---|---|
| C21 | 0.2298 | 0.2776 | 0.3376 | 4.4 |
| C22 | 0.2492 | 0.3487 | 0.3726 | 4.0 |
| C23 | 0.2378 | 0.4384 | 0.3690 | 5.0 |
| C24 | 0.2059 | 0.4565 | 0.3317 | 4.9 |
| C26 | 0.3075 | 0.3768 | 0.4173 | 5.4 |
| C27 | 0.3369 | 0.3517 | 0.4703 | 6.8 |
| C28 | 0.3386 | 0.2854 | 0.5163 | 6.5 |
| C29 | 0.3111 | 0.2351 | 0.5143 | 5.9 |
| C30 | 0.2830 | 0.2569 | 0.4655 | 5.0 |
| CL2 | 0.0820 | −0.3293 | 0.4983 | 5.6 |
| O48 | 0.1355 | −0.3140 | 0.3362 | 5.7 |
| O66 | 0.2699 | −0.3890 | 0.4679 | 5.4 |
| N41 | 0.0678 | −0.3119 | 0.2446 | 3.9 |
| N42 | 0.0415 | −0.2967 | 0.1896 | 4.0 |
| N47 | 0.1490 | −0.2393 | 0.2530 | 4.0 |
| O57 | 0.0328 | −0.1413 | 0.0553 | 5.5 |
| N58 | 0.0024 | −0.2675 | 0.0563 | 4.8 |
| N65 | 0.2810 | −0.2819 | 0.3985 | 4.1 |
| C43 | 0.0514 | −0.2437 | 0.1479 | 3.7 |
| C44 | 0.0840 | −0.2242 | 0.1750 | 3.8 |
| C45 | 0.1075 | −0.1719 | 0.1510 | 4.4 |
| C46 | 0.1402 | −0.2180 | 0.1797 | 5.1 |
| C48 | 0.1277 | −0.2767 | 0.2807 | 3.9 |
| C49 | 0.0942 | −0.2695 | 0.2364 | 3.7 |
| C50 | 0.0632 | −0.3603 | 0.3003 | 3.6 |
| C51 | 0.0760 | −0.3267 | 0.3655 | 3.8 |
| C52 | 0.0682 | −0.3731 | 0.4159 | 4.1 |
| C53 | 0.0488 | −0.4500 | 0.4036 | 4.5 |
| C54 | 0.0363 | −0.4829 | 0.3377 | 4.9 |
| C55 | 0.0434 | −0.4378 | 0.2853 | 4.5 |
| C56 | 0.0281 | −0.2135 | 0.0824 | 3.9 |
| C59 | 0.1828 | −0.2493 | 0.2902 | 3.9 |
| C60 | 0.2025 | −0.2930 | 0.2597 | 4.8 |
| C61 | 0.2347 | −0.3036 | 0.2960 | 4.7 |
| C62 | 0.2469 | −0.2708 | 0.3613 | 4.0 |
| C63 | 0.2272 | −0.2262 | 0.3915 | 4.3 |
| C64 | 0.1952 | −0.2145 | 0.3556 | 4.2 |
| C66 | 0.2903 | −0.3442 | 0.4519 | 4.3 |
| C67 | 0.3243 | −0.3533 | 0.4856 | 5.0 |
| C68 | 0.3451 | −0.3025 | 0.4660 | 5.7 |
| C69 | 0.3339 | −0.2385 | 0.4108 | 5.7 |
| C70 | 0.3025 | −0.2306 | 0.3785 | 4.8 |
| CL3 | 0.0889 | 0.0000 | 0.5092 | 6.0 |
| O88 | 0.1407 | −0.0225 | 0.3482 | 5.4 |
| O106 | 0.3093 | 0.0778 | 0.3670 | 6.8 |
| N81 | 0.0745 | 0.0071 | 0.2558 | 3.8 |
| N82 | 0.0492 | 0.0309 | 0.2008 | 4.0 |
| N87 | 0.1585 | 0.0543 | 0.2712 | 3.8 |
| O97 | 0.0450 | 0.1918 | 0.0730 | 5.6 |
| N98 | 0.0128 | 0.0693 | 0.0685 | 4.9 |
| N105 | 0.2874 | −0.0044 | 0.4344 | 3.8 |
| C83 | 0.0615 | 0.0814 | 0.1617 | 3.5 |
| C84 | 0.0947 | 0.0910 | 0.1910 | 3.7 |
| C85 | 0.1206 | 0.1368 | 0.1711 | 4.2 |
| C86 | 0.1513 | 0.0796 | 0.1990 | 4.1 |
| C88 | 0.1351 | 0.0211 | 0.2952 | 4.0 |
| C89 | 0.1026 | 0.0417 | 0.2506 | 3.6 |
| C90 | 0.0674 | −0.0351 | 0.3110 | 3.7 |
| C91 | 0.0819 | −0.0031 | 0.3766 | 3.9 |
| C92 | 0.0720 | −0.0411 | 0.4269 | 4.1 |
| C93 | 0.0484 | −0.1078 | 0.4139 | 4.4 |
| C94 | 0.0343 | −0.1389 | 0.3483 | 4.8 |
| C95 | 0.0436 | −0.1024 | 0.2961 | 4.4 |
| C96 | 0.0392 | 0.1190 | 0.0970 | 3.8 |
| C99 | 0.1915 | 0.0400 | 0.3116 | 3.8 |
| C100 | 0.2015 | 0.0604 | 0.3808 | 4.1 |
| C101 | 0.2330 | 0.0463 | 0.4200 | 4.0 |
| C102 | 0.2550 | 0.0132 | 0.3905 | 3.7 |
| C103 | 0.2453 | −0.0042 | 0.3218 | 4.2 |
| C104 | 0.2136 | 0.0082 | 0.2822 | 4.1 |
| C106 | 0.3133 | 0.0332 | 0.4193 | 4.7 |
| C107 | 0.3442 | 0.0142 | 0.4691 | 5.3 |
| C108 | 0.3473 | −0.0361 | 0.5254 | 5.6 |
| C109 | 0.3206 | −0.0733 | 0.5376 | 5.3 |
| C110 | 0.2911 | −0.0561 | 0.4924 | 4.5 |
| H181 | 0.0009 | 0.3424 | 0.0914 | 6.2 |
| H182 | −0.0127 | 0.4250 | 0.0183 | 6.2 |
| H581 | −0.0006 | −0.3306 | 0.0827 | 5.8 |
| H981 | 0.0089 | 0.0044 | 0.0918 | 6.0 |
| H982 | −0.0051 | 0.0926 | 0.0224 | 6.0 |
| H582 | −0.0183 | −0.2244 | 0.0512 | 4.0 |

Approximate error in x, y, z are .001, .0003, .0003

TABLE 3a

Positional Parameters and Isotropic Equivalent Temperature Factors Form N-1 at −50° C.

| Atom | x | y | z | B(iso) |
|---|---|---|---|---|
| CL1 | 0.0851 | 0.3260 | 0.5044 | 4.0 |
| CL2 | 0.0817 | −0.3307 | 0.5005 | 3.2 |
| CL3 | 0.0891 | −0.0024 | 0.5115 | 3.5 |
| O8 | 0.1369 | 0.2946 | 0.3262 | 3.4 |
| O17 | 0.0391 | 0.5245 | 0.0641 | 3.8 |
| O26 | 0.3062 | 0.4358 | 0.3737 | 4.5 |
| O48 | 0.1358 | −0.3101 | 0.3386 | 3.4 |
| O57 | 0.0325 | −0.1389 | 0.0558 | 2.9 |
| O66 | 0.2703 | −0.3905 | 0.4672 | 2.6 |
| O88 | 0.1411 | −0.0227 | 0.3496 | 3.1 |
| O97 | 0.0445 | 0.1954 | 0.0743 | 3.1 |
| O106 | 0.3102 | 0.0784 | 0.3673 | 3.9 |
| N1 | 0.0699 | 0.3417 | 0.2499 | 2.1 |
| N2 | 0.0439 | 0.3625 | 0.1965 | 2.2 |
| N7 | 0.1530 | 0.4054 | 0.2642 | 2.0 |
| N18 | 0.0058 | 0.4031 | 0.0650 | 2.7 |
| N25 | 0.2811 | 0.3269 | 0.4187 | 1.9 |
| N41 | 0.0679 | −0.3103 | 0.2455 | 1.7 |
| N42 | 0.0412 | −0.2974 | 0.1902 | 2.0 |
| N47 | 0.1491 | −0.2363 | 0.2535 | 2.2 |
| N58 | 0.0026 | −0.2687 | 0.0567 | 2.2 |
| N65 | 0.2811 | −0.2810 | 0.3982 | 1.9 |
| N81 | 0.0746 | 0.0071 | 0.2559 | 1.9 |
| N82 | 0.0492 | 0.0309 | 0.2011 | 1.9 |
| N87 | 0.1591 | 0.0572 | 0.2731 | 2.0 |
| N98 | 0.0134 | 0.0689 | 0.0686 | 2.2 |
| N105 | 0.2880 | −0.0050 | 0.4354 | 1.8 |
| C3 | 0.0554 | 0.4170 | 0.1559 | 1.8 |
| C4 | 0.0884 | 0.4303 | 0.1848 | 1.7 |
| C5 | 0.1133 | 0.4814 | 0.1613 | 2.8 |
| C6 | 0.1437 | 0.4917 | 0.2251 | 2.8 |
| C8 | 0.1304 | 0.3569 | 0.2835 | 2.8 |
| C9 | 0.0973 | 0.3828 | 0.2453 | 1.8 |
| C10 | 0.0641 | 0.2943 | 0.3053 | 1.9 |
| C11 | 0.0788 | 0.3267 | 0.3714 | 1.9 |
| C12 | 0.0696 | 0.2834 | 0.4217 | 2.7 |
| C13 | 0.0483 | 0.2077 | 0.4091 | 2.4 |
| C14 | 0.0345 | 0.1785 | 0.3427 | 2.5 |
| C15 | 0.0424 | 0.2219 | 0.2911 | 2.5 |
| C16 | 0.0326 | 0.4535 | 0.0908 | 2.5 |
| C19 | 0.1865 | 0.3867 | 0.2996 | 1.5 |
| C20 | 0.1976 | 0.2972 | 0.3008 | 2.1 |
| C21 | 0.2298 | 0.2772 | 0.3380 | 2.1 |
| C22 | 0.2493 | 0.3499 | 0.3717 | 1.5 |
| C23 | 0.2385 | 0.4399 | 0.3684 | 1.9 |
| C24 | 0.2062 | 0.4578 | 0.3308 | 2.3 |
| C26 | 0.3079 | 0.3766 | 0.4184 | 2.8 |
| C27 | 0.3374 | 0.3518 | 0.4716 | 3.9 |
| C28 | 0.3381 | 0.2827 | 0.5167 | 3.6 |
| C29 | 0.3107 | 0.2344 | 0.5139 | 3.4 |
| C30 | 0.2831 | 0.2554 | 0.4648 | 2.6 |
| C43 | 0.0510 | −0.2413 | 0.1485 | 1.8 |
| C44 | 0.0843 | −0.2235 | 0.1755 | 1.9 |
| C45 | 0.1076 | −0.1677 | 0.1526 | 2.2 |
| C46 | 0.1403 | −0.2146 | 0.1796 | 2.2 |

TABLE 3a-continued

Positional Parameters and Isotropic Equivalent Temperature Factors Form N-1 at −50° C.

| Atom | x | y | z | B(iso) |
|---|---|---|---|---|
| C48 | 0.1271 | −0.2768 | 0.2823 | 2.1 |
| C49 | 0.0942 | −0.2664 | 0.2371 | 1.9 |
| C50 | 0.0627 | −0.3610 | 0.2999 | 1.5 |
| C51 | 0.0759 | −0.3260 | 0.3671 | 1.9 |
| C52 | 0.0681 | −0.3729 | 0.4171 | 2.0 |
| C53 | 0.0486 | −0.4512 | 0.4051 | 2.4 |
| C54 | 0.0353 | −0.4836 | 0.3369 | 2.8 |
| C55 | 0.0429 | −0.4372 | 0.2856 | 2.2 |
| C56 | 0.0278 | −0.2133 | 0.0823 | 2.0 |
| C59 | 0.1828 | −0.2461 | 0.2904 | 2.3 |
| C60 | 0.2031 | −0.2907 | 0.2584 | 2.4 |
| C61 | 0.2353 | −0.3010 | 0.2953 | 2.5 |
| C62 | 0.2472 | −0.2714 | 0.3609 | 2.0 |
| C63 | 0.2275 | −0.2235 | 0.3926 | 2.2 |
| C64 | 0.1953 | −0.2127 | 0.3576 | 2.2 |
| C66 | 0.2902 | −0.3425 | 0.4522 | 2.0 |
| C67 | 0.3247 | −0.3515 | 0.4852 | 2.8 |
| C68 | 0.3456 | −0.2976 | 0.4645 | 3.6 |
| C69 | 0.3346 | −0.2354 | 0.4107 | 3.0 |
| C70 | 0.3026 | −0.2284 | 0.3783 | 2.7 |
| C83 | 0.0614 | 0.0843 | 0.1622 | 1.7 |
| C84 | 0.0948 | 0.0918 | 0.1913 | 1.5 |
| C85 | 0.1211 | 0.1407 | 0.1724 | 1.7 |
| C86 | 0.1515 | 0.0801 | 0.1994 | 1.9 |
| C88 | 0.1355 | 0.0203 | 0.2952 | 2.1 |
| C89 | 0.1026 | 0.0446 | 0.2510 | 2.0 |
| C90 | 0.0672 | −0.0352 | 0.3123 | 1.7 |
| C91 | 0.0819 | −0.0037 | 0.3779 | 2.0 |
| C92 | 0.0721 | −0.0424 | 0.4293 | 2.2 |
| C93 | 0.0483 | −0.1104 | 0.4158 | 2.2 |
| C94 | 0.0343 | −0.1394 | 0.3490 | 2.6 |
| C95 | 0.0435 | −0.1017 | 0.2964 | 2.4 |
| C96 | 0.0389 | 0.1192 | 0.0962 | 1.7 |
| C99 | 0.1917 | 0.0425 | 0.3124 | 1.9 |
| C100 | 0.2019 | 0.0609 | 0.3818 | 2.0 |
| C101 | 0.2328 | 0.0471 | 0.4213 | 2.0 |
| C102 | 0.2558 | 0.0118 | 0.3925 | 2.0 |
| C103 | 0.2461 | −0.0033 | 0.3211 | 2.2 |
| C104 | 0.2138 | 0.0110 | 0.2819 | 2.0 |
| C106 | 0.3142 | 0.0339 | 0.4202 | 2.7 |
| C107 | 0.3447 | 0.0163 | 0.4698 | 2.6 |
| C108 | 0.3478 | −0.0346 | 0.5267 | 3.2 |
| C109 | 0.3204 | −0.0739 | 0.5392 | 2.9 |
| C110 | 0.2912 | −0.0565 | 0.4933 | 2.3 |
| H181 | 0.0016 | 0.3415 | 0.0920 | 3.6 |
| H182 | −0.0121 | 0.4224 | 0.0173 | 3.6 |
| H581 | 0.0001 | −0.3330 | 0.0820 | 3.2 |
| H582 | −0.0165 | −0.2479 | 0.0107 | 3.2 |
| H981 | 0.0105 | 0.0036 | 0.0919 | 3.0 |
| H982 | −0.0050 | 0.0909 | 0.0217 | 3.0 |

TABLE 4

Positional Parameters and Isotropic Equivalent Temperature Factor Form N-2 at room temperature

| Atom | x | y | z | B (iso) |
|---|---|---|---|---|
| CL1 | −0.135841 | −0.286717 | −0.094687 | 7.0 |
| CL2 | 0.308306 | 0.289608 | 0.925413 | 7.3 |
| O8 | −0.180684 | −0.553617 | 0.077453 | 5.6 |
| O17 | 0.009131 | −0.027751 | 0.367246 | 5.6 |
| O26 | −0.444446 | −0.547937 | −0.064208 | 7.7 |
| O48 | 0.353429 | 0.546521 | 0.752078 | 6.2 |
| O57 | 0.162822 | 0.050250 | 0.460989 | 9.0 |
| O66 | 0.620053 | −0.050755 | 0.722031 | 7.0 |
| N1 | −0.056121 | −0.389894 | 0.158118 | 5.1 |
| N2 | −0.003828 | −0.346977 | 0.210536 | 5.6 |
| N7 | −0.199990 | −0.296448 | 0.159041 | 4.2 |
| N18 | 0.079497 | −0.250428 | 0.339830 | 7.8 |
| N25 | −0.440023 | −0.256272 | 0.027668 | 3.6 |
| N41 | 0.227176 | 0.375554 | 0.673430 | 4.3 |
| N42 | 0.178579 | 0.312867 | 0.617060 | 4.7 |
| N47 | 0.368032 | 0.271293 | 0.672441 | 5.7 |
| N58 | 0.093937 | 0.208036 | 0.491185 | 4.5 |
| N65 | 0.613256 | 0.221664 | 0.809980 | 5.3 |
| C3 | −0.018504 | −0.250763 | 0.260794 | 3.7 |
| C4 | −0.077398 | −0.251166 | 0.240606 | 4.9 |
| C5 | −0.117716 | −0.185048 | 0.272564 | 5.3 |
| C6 | −0.177927 | −0.108086 | 0.220878 | 5.0 |
| C8 | −0.164648 | −0.405370 | 0.128666 | 5.0 |
| C9 | −0.103337 | −0.332311 | 0.169699 | 4.4 |
| C10 | −0.050597 | −0.465026 | 0.100091 | 4.8 |
| C11 | −0.090182 | −0.340321 | 0.038024 | 4.0 |
| C12 | −0.085777 | −0.413661 | −0.019688 | 3.6 |
| C13 | −0.036756 | −0.597854 | −0.014695 | 6.3 |
| C14 | 0.005774 | −0.710337 | 0.047541 | 6.4 |
| C15 | −0.002972 | −0.649451 | 0.100182 | 4.4 |
| C16 | 0.029106 | −0.176073 | 0.330744 | 5.0 |
| C19 | −0.259381 | −0.293483 | 0.118954 | 5.0 |
| C20 | −0.291078 | −0.441986 | 0.152128 | 5.0 |
| C21 | −0.351216 | −0.432197 | 0.119188 | 5.0 |
| C22 | −0.375655 | −0.290739 | 0.060616 | 4.7 |
| C23 | −0.347355 | −0.118093 | 0.024767 | 6.0 |
| C24 | −0.285645 | −0.157393 | 0.058200 | 4.8 |
| C26 | −0.468973 | −0.365812 | −0.035584 | 4.4 |
| C27 | −0.530692 | −0.331465 | −0.068999 | 5.6 |
| C28 | −0.557164 | −0.193666 | −0.038159 | 5.9 |
| C29 | −0.525554 | −0.069547 | 0.026983 | 6.0 |
| C30 | −0.463141 | −0.078130 | 0.065993 | 5.0 |
| C43 | 0.194036 | 0.242736 | 0.571113 | 5.3 |
| C44 | 0.252850 | 0.240736 | 0.594478 | 3.6 |
| C45 | 0.289189 | 0.202874 | 0.559973 | 5.0 |
| C46 | 0.346467 | 0.064822 | 0.610082 | 6.1 |
| C48 | 0.333197 | 0.391199 | 0.698071 | 5.0 |
| C49 | 0.271483 | 0.320215 | 0.655702 | 4.3 |
| C50 | 0.223989 | 0.457358 | 0.733977 | 4.5 |
| C51 | 0.267853 | 0.357528 | 0.795195 | 5.7 |
| C52 | 0.254582 | 0.439889 | 0.848257 | 6.f5 |
| C53 | 0.208703 | 0.616242 | 0.845896 | 6.0 |
| C54 | 0.170704 | 0.711142 | 0.786299 | 5.1 |
| C55 | 0.175781 | 0.634200 | 0.725267 | 5.8 |
| C56 | 0.151595 | 0.145768 | 0.505108 | 5.6 |
| C59 | 0.433366 | 0.282037 | 0.707701 | 4.7 |
| C60 | 0.460060 | 0.114791 | 0.769749 | 5.3 |
| C61 | 0.516566 | 0.119382 | 0.799476 | 4.7 |
| C62 | 0.552226 | 0.226618 | 0.773971 | 4.6 |
| C63 | 0.524787 | 0.407839 | 0.711379 | 5.2 |
| C64 | 0.465724 | 0.421596 | 0.680006 | 5.2 |
| C66 | 0.646462 | 0.096428 | 0.780012 | 4.4 |
| C67 | 0.704829 | 0.071429 | 0.811131 | 7.4 |
| C68 | 0.731420 | 0.182248 | 0.874211 | 7.8 |
| C69 | 0.695375 | 0.333003 | 0.902910 | 6.6 |
| C70 | 0.638527 | 0.369656 | 0.874228 | 6.3 |
| H181 | 0.082900 | −0.372500 | 0.303200 | 7.0 |
| H182 | 0.111100 | −0.138100 | 0.382200 | 7.0 |
| H581 | 0.076700 | 0.301300 | 0.528100 | 7.0 |
| H582 | 0.054500 | 0.179300 | 0.440700 | 7.1 |

Average errors for x, y, z are .0004, .003, .0007

TABLE 5

Positional Parameters, Occupancy Factors and Isotropic Equivalent Temperature Factors Form .5SBU-4 at +22° C.

| Atom | x | Y | z | Occupancy | B(iso) |
|---|---|---|---|---|---|
| CL1 | 0.1371 | 0.9122 | 0.4673 | 1.00 | 13.1 |
| O8 | 0.2755 | 0.6426 | 0.2992 | 1.00 | 3.8 |
| O16 | 0.7953 | 0.3504 | 0.4288 | 1.00 | 4.8 |
| O25 | −0.0135 | 0.3813 | 0.0604 | 1.00 | 7.9 |
| N1 | 0.5081 | 0.6259 | 0.3895 | 1.00 | 3.1 |

TABLE 5-continued

Positional Parameters, Occupancy Factors and Isotropic Equivalent Temperature Factors Form .5SBU-4 at +22° C.

| Atom | x | Y | z | Occupancy | B(iso) |
|---|---|---|---|---|---|
| N2 | 0.6264 | 0.5904 | 0.4172 | 1.00 | 3.4 |
| N7 | 0.3167 | 0.4851 | 0.3124 | 1.00 | 3.2 |
| N17 | 0.8526 | 0.4699 | 0.4759 | 1.00 | 4.3 |
| N24 | −0.1272 | 0.4851 | 0.1561 | 1.00 | 4.0 |
| C3 | 0.6514 | 0.4987 | 0.4137 | 1.00 | 3.2 |
| C4 | 0.5484 | 0.4739 | 0.3825 | 1.00 | 3.2 |
| C5 | 0.5253 | 0.3857 | 0.3604 | 1.00 | 3.9 |
| C6 | 0.3788 | 0.3997 | 0.3610 | 1.00 | 3.9 |
| C8 | 0.3404 | 0.5681 | 0.3248 | 1.00 | 2.9 |
| C9 | 0.4587 | 0.5566 | 0.3677 | 1.00 | 3.0 |
| C10 | 0.4548 | 0.7246 | 0.3829 | 1.00 | 3.4 |
| C11 | 0.3352 | 0.7648 | 0.4239 | 1.00 | 4.6 |
| C12 | 0.2882 | 0.8591 | 0.4159 | 1.00 | 6.2 |
| C13 | 0.3579 | 0.9145 | 0.3681 | 1.00 | 6.2 |
| C14 | 0.4782 | 0.8716 | 0.3291 | 1.00 | 5.9 |
| C15 | 0.5281 | 0.7779 | 0.3359 | 1.00 | 4.7 |
| C16 | 0.7734 | 0.4335 | 0.4401 | 1.00 | 3.5 |
| C18 | 0.2058 | 0.4850 | 0.2712 | 1.00 | 3.2 |
| C19 | 0.1868 | 0.5280 | 0.1927 | 1.00 | 3.7 |
| C20 | 0.0788 | 0.5271 | 0.1536 | 1.00 | 4.1 |
| C21 | −0.0094 | 0.4814 | 0.1945 | 1.00 | 3.6 |
| C22 | 0.0100 | 0.4349 | 0.2705 | 1.00 | 3.8 |
| C23 | 0.1173 | 0.4375 | 0.3108 | 1.00 | 3.6 |
| C25 | −0.1188 | 0.4305 | 0.0882 | 1.00 | 5.2 |
| C26 | −0.2431 | 0.4384 | 0.0563 | 1.00 | 6.0 |
| C27 | −0.3536 | 0.4922 | 0.0905 | 1.00 | 6.0 |
| C28 | −0.3560 | 0.5454 | 0.1597 | 1.00 | 6.4 |
| C29 | −0.2422 | 0.5408 | 0.1911 | 1.00 | 5.4 |
| CL2 | 1.0582 | −0.2150 | 0.0516 | 1.00 | 8.1 |
| O38 | 0.5757 | 0.0366 | 0.2274 | 1.00 | 5.3 |
| O55 | 0.1058 | 0.3485 | 0.5156 | 1.00 | 4.3 |
| N31 | 0.6557 | 0.0578 | 0.0452 | 1.00 | 4.4 |
| N32 | 0.6900 | 0.0994 | −0.0274 | 1.00 | 4.5 |
| N37 | 0.4225 | 0.1756 | 0.2133 | 1.00 | 4.5 |
| N54 | 0.1964 | 0.1965 | 0.5492 | 1.00 | 4.0 |
| C33 | 0.6252 | 0.1883 | −0.0224 | 1.00 | 4.0 |
| C34 | 0.5455 | 0.2045 | 0.0546 | 1.00 | 4.0 |
| C35 | 0.4501 | 0.2869 | 0.0930 | 1.00 | 5.0 |
| C36 | 0.3519 | 0.2490 | 0.1536 | 1.00 | 5.1 |
| C38 | 0.5237 | 0.1039 | 0.1848 | 1.00 | 4.2 |
| C39 | 0.5682 | 0.1202 | 0.0951 | 1.00 | 4.0 |
| C40 | 0.7080 | −0.0398 | 0.0592 | 1.00 | 4.5 |
| C41 | 0.8415 | −0.0755 | 0.0483 | 1.00 | 5.3 |
| C42 | 0.8919 | −0.1718 | 0.0596 | 1.00 | 5.4 |
| C43 | 0.8116 | −0.2274 | 0.0792 | 1.00 | 5.6 |
| C44 | 0.6784 | −0.1904 | 0.0911 | 1.00 | 6.2 |
| C45 | 0.6261 | −0.0970 | 0.0824 | 1.00 | 5.4 |
| C46 | 0.6411 | 0.2569 | −0.0930 | 1.00 | 4.4 |
| N47 | 0.6871 | 0.2217 | −0.1669 | 1.00 | 5.8 |
| O46 | 0.6104 | 0.3398 | −0.0793 | 1.00 | 5.3 |
| C48 | 0.3672 | 0.1729 | 0.2994 | 1.00 | 4.1 |
| C49 | 0.2323 | 0.1933 | 0.3152 | 1.00 | 4.5 |
| C50 | 0.1764 | 0.1995 | 0.3991 | 1.00 | 4.4 |
| C51 | 0.2559 | 0.1844 | 0.4634 | 1.00 | 4.0 |
| C52 | 0.3899 | 0.1614 | 0.4470 | 1.00 | 4.3 |
| C53 | 0.4466 | 0.1555 | 0.3645 | 1.00 | 4.2 |
| C55 | 0.1196 | 0.2838 | 0.5695 | 1.00 | 3.9 |
| C56 | 0.0615 | 0.2901 | 0.6542 | 1.00 | 5.9 |
| C57 | 0.0837 | 0.2185 | 0.7101 | 1.00 | 6.6 |
| C58 | 0.1672 | 0.1336 | 0.6875 | 1.00 | 6.8 |
| C59 | 0.2212 | 0.1237 | 0.6071 | 1.00 | 5.6 |
| C95 | 0.0821 | 0.0157 | 0.2131 | 0.75 | 11.5 |
| C96 | −0.0335 | 0.0847 | 0.2368 | 0.75 | 15.1 |
| C97 | −0.1987 | 0.2308 | 0.2132 | 0.75 | 12.0 |
| C98 | −0.0723 | 0.1657 | 0.1871 | 0.75 | 10.1 |
| O99 | 0.0405 | 0.2033 | 0.1647 | 0.75 | 8.2 |
| H171 | 0.8317 | 0.5455 | 0.4861 | 1.00 | 3.6 |
| H172 | 0.9450 | 0.4274 | 0.4975 | 1.00 | 3.6 |
| H991 | 0.0073 | 0.2694 | 0.1264 | 0.75 | 4.8 |

Average errors for x, y, z are .003, .002, .003

TABLE 5a

Positional Parameters, Occupancy Factors and Isotropic Equivalent Temperature Factors Form .5SBU-4 at −50° C.

| Atom | x | Y | z | Occupancy | B(iso) |
|---|---|---|---|---|---|
| CL1 | 0.1406 | 0.9124 | 0.4721 | 1.00 | 9.4 |
| O8 | 0.2748 | 0.6424 | 0.3017 | 1.00 | 2.7 |
| O16 | 0.7956 | 0.3499 | 0.4261 | 1.00 | 3.3 |
| O25 | −0.0179 | 0.3812 | 0.0592 | 1.00 | 5.0 |
| N1 | 0.5092 | 0.6259 | 0.3912 | 1.00 | 2.2 |
| N2 | 0.6289 | 0.5904 | 0.4183 | 1.00 | 2.4 |
| N7 | 0.3167 | 0.4839 | 0.3127 | 1.00 | 2.2 |
| N17 | 0.8538 | 0.4703 | 0.4764 | 1.00 | 3.1 |
| N24 | −0.1302 | 0.4862 | 0.1560 | 1.00 | 2.8 |
| C3 | 0.6526 | 0.4984 | 0.4132 | 1.00 | 2.3 |
| C4 | 0.5485 | 0.4732 | 0.3822 | 1.00 | 2.2 |
| C5 | 0.5249 | 0.3847 | 0.3593 | 1.00 | 2.8 |
| C6 | 0.3783 | 0.3980 | 0.3605 | 1.00 | 2.7 |
| C8 | 0.3402 | 0.5676 | 0.3259 | 1.00 | 2.1 |
| C9 | 0.4586 | 0.5562 | 0.3692 | 1.00 | 2.1 |
| C10 | 0.4574 | 0.7242 | 0.3846 | 1.00 | 2.4 |
| C11 | 0.3378 | 0.7650 | 0.4274 | 1.00 | 3.3 |
| C12 | 0.2920 | 0.8595 | 0.4193 | 1.00 | 4.3 |
| C13 | 0.3608 | 0.9152 | 0.3707 | 1.00 | 4.4 |
| C14 | 0.4820 | 0.8721 | 0.3292 | 1.00 | 4.2 |
| C15 | 0.5320 | 0.7774 | 0.3359 | 1.00 | 3.3 |
| C16 | 0.7746 | 0.4327 | 0.4387 | 1.00 | 2.5 |
| C18 | 0.2050 | 0.4838 | 0.2709 | 1.00 | 2.2 |
| C19 | 0.1868 | 0.5294 | 0.1926 | 1.00 | 2.6 |
| C20 | 0.0770 | 0.5294 | 0.1537 | 1.00 | 2.8 |
| C21 | −0.0112 | 0.4816 | 0.1937 | 1.00 | 2.5 |
| C22 | 0.0078 | 0.4334 | 0.2696 | 1.00 | 2.7 |
| C23 | 0.1167 | 0.4351 | 0.3101 | 1.00 | 2.5 |
| C25 | −0.1236 | 0.4322 | 0.0870 | 1.00 | 3.5 |
| C26 | −0.2481 | 0.4409 | 0.0553 | 1.00 | 4.0 |
| C27 | −0.3594 | 0.4963 | 0.0909 | 1.00 | 4.2 |
| C28 | −0.3595 | 0.5502 | 0.1609 | 1.00 | 4.4 |
| C29 | −0.2441 | 0.5430 | 0.1913 | 1.00 | 3.7 |
| CL2 | 1.0621 | −0.2129 | 0.0488 | 1.00 | 5.4 |
| O38 | 0.5796 | 0.0366 | 0.2275 | 1.00 | 3.8 |
| O55 | 0.1046 | 0.3481 | 0.5157 | 1.00 | 3.0 |
| N31 | 0.6567 | 0.0563 | 0.0426 | 1.00 | 3.2 |
| N32 | 0.6908 | 0.0978 | −0.0315 | 1.00 | 3.2 |
| N37 | 0.4237 | 0.1742 | 0.2130 | 1.00 | 3.2 |
| N54 | 0.1932 | 0.1960 | 0.5510 | 1.00 | 2.9 |
| C33 | 0.6263 | 0.1874 | −0.0265 | 1.00 | 3.0 |
| C34 | 0.5474 | 0.2033 | 0.0516 | 1.00 | 2.9 |
| C35 | 0.4518 | 0.2854 | 0.0917 | 1.00 | 3.7 |
| C36 | 0.3541 | 0.2471 | 0.1534 | 1.00 | 3.7 |
| C38 | 0.5262 | 0.1033 | 0.1838 | 1.00 | 3.0 |
| C39 | 0.5701 | 0.1187 | 0.0933 | 1.00 | 3.0 |
| C40 | 0.7092 | −0.0410 | 0.0571 | 1.00 | 3.2 |
| C41 | 0.8434 | −0.0755 | 0.0460 | 1.00 | 3.8 |
| C42 | 0.8949 | −0.1718 | 0.0575 | 1.00 | 3.6 |
| C43 | 0.8148 | −0.2290 | 0.0783 | 1.00 | 4.0 |
| C44 | 0.6807 | −0.1939 | 0.0909 | 1.00 | 4.0 |
| C45 | 0.6266 | −0.0986 | 0.0806 | 1.00 | 3.7 |
| C46 | 0.6427 | 0.2551 | −0.0968 | 1.00 | 3.0 |
| N47 | 0.6896 | 0.2198 | −0.1718 | 1.00 | 4.2 |
| O46 | 0.6114 | 0.3388 | −0.0834 | 1.00 | 3.6 |
| C48 | 0.3670 | 0.1710 | 0.2992 | 1.00 | 2.9 |
| C49 | 0.2323 | 0.1906 | 0.3163 | 1.00 | 3.3 |
| C50 | 0.1751 | 0.1965 | 0.3994 | 1.00 | 3.1 |
| C51 | 0.2544 | 0.1826 | 0.4641 | 1.00 | 2.8 |
| C52 | 0.3887 | 0.1602 | 0.4478 | 1.00 | 3.1 |
| C53 | 0.4464 | 0.1540 | 0.3655 | 1.00 | 3.0 |
| C55 | 0.1169 | 0.2843 | 0.5709 | 1.00 | 2.7 |
| C56 | 0.0582 | 0.2927 | 0.6567 | 1.00 | 4.2 |
| C57 | 0.0788 | 0.2217 | 0.7136 | 1.00 | 4.7 |
| C58 | 0.1617 | 0.1346 | 0.6913 | 1.00 | 4.9 |
| C59 | 0.2169 | 0.1233 | 0.6093 | 1.00 | 4.1 |
| C95 | 0.0817 | 0.0159 | 0.2147 | 0.75 | 6.9 |
| C96 | −0.0333 | 0.0867 | 0.2456 | 0.75 | 7.5 |
| C97 | −0.1991 | 0.2339 | 0.2145 | 0.75 | 6.4 |
| C98 | −0.0721 | 0.1654 | 0.1872 | 0.75 | 6.3 |
| O99 | 0.0385 | 0.2070 | 0.1650 | 0.75 | 4.7 |
| H171 | 0.8317 | 0.5455 | 0.4861 | 1.00 | 3.6 |
| H471 | 0.7048 | 0.2650 | −0.2282 | 1.00 | 4.9 |
| H172 | 0.9450 | 0.4274 | 0.4975 | 0.75 | 3.6 |

TABLE 5a-continued

Positional Parameters, Occupancy Factors and Isotropic Equivalent
Temperature Factors Form .5SBU-4 at −50° C.

| Atom | x | Y | z | Occupancy | B(iso) |
|---|---|---|---|---|---|
| H472 | 0.7127 | 0.1451 | −0.1820 | 1.00 | 4.9 |
| H991 | 0.0073 | 0.2694 | 0.1264 | 0.75 | 4.8 |

Average errors for x, y, z are .003, .002, .003

Numerous modifications and variations of the present invention are possible in light of the above teachings. It is therefore to be understood that within the scope of the appended claims, the invention may be practiced otherwise than as specifically described herein.

What is claimed is:

1. Crystalline Form N-3 of 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide, which is characterized by SSNMR substantially in accordance with that shown in FIG. 1.

2. Crystalline Form N-3 according to claim 1, in substantially pure form.

3. Crystalline Form N-3 according to claim 1, wherein substantially pure is greater than 90 percent pure.

4. Crystalline Form N-3 according to claim 1, which is characterized by a powder X-ray diffraction pattern substantially in accordance with that shown in FIG. 2.

5. Crystalline Form N-3 according to claim 1 having a powder X-ray diffraction pattern comprising the following 2θ values (CuKα λ=1.5418 Å): 8.6±0.2, 11.4±0.2, 12.3±0.2 and 15.6±0.2, at about 22° C.

6. Crystalline Form N-3 according to claim 1, which is characterized by a differential scanning calorimetry thermogram having a peak onset at about 245-253° C.

7. Crystalline Form N-1 of 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide, which is characterized by unit cell parameters substantially equal to the following:

| Cell dimensions: | a = 44.272(1) Å |
| | b = 14.3594(4) Å |
| | c = 20.9164(6) Å |
| | β = 109.36(1) |
| Space group | C2/c |
| Molecules/asymmetric unit | 3 | wherein the crystalline form is at about +22° C.

8. Crystalline Form N-1 according to claim 7, which is characterized by fractional atomic coordinates substantially as listed in Table 3.

9. Crystalline Form N-1 according to claim 7, which is characterized by a powder X-ray diffraction pattern substantially in accordance with that shown in FIG. 3.

10. Crystalline Form N-1 according to claim 7 having a powder X-ray diffraction pattern comprising the following 2θ values (CuKα λ=1.5418 Å): 4.3±0.2, 10.1±0.2, 14.3±0.2 and 17.1±0.2, at about 22° C.

11. Crystalline Form N-2 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide, which is characterized by unit cell parameters substantially equal to the following:

| Cell dimensions: | a = 26.004(1) Å |
| | b = 4.063(1) Å |
| | c = 22.653(1) Å |
| | β = 115.95(1) |
| Space group | Pc |
| Molecules/asymmetric unit | 2 | wherein the crystalline form is at about +22° C.

12. Crystalline Form N-2 according to claim 11, which is characterized by fractional atomic coordinates substantially as listed in Table 4.

13. Crystalline Form N-2 according to claim 11, which is characterized by a powder X-ray diffraction pattern substantially in accordance with that shown in FIG. 4.

14. Crystalline Form N-2 according to claim 11 having a powder X-ray diffraction pattern comprising the following 2θ values (CuKα λ=1.5418 Å): 8.8±0.2, 11.4±0.2, 13.9±0.2, 15.7±0.2 and 22.4±0.2, at about 22° C.

15. Crystalline Form N-2 according to claim 11, which is characterized by a differential scanning calorimetry thermogram having a peak onset at about 254-258° C.

16. Crystalline P-1 form of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide, which is characterized by an X-ray powder diffraction pattern substantially in accordance with that shown in FIG. 5.

17. Crystalline P-1 form according to claim 16 having a powder X-ray diffraction pattern comprising the following 2θ values (CuKα λ=1.5418 Å): 5.5±0.2, 11.1±0.2, 15.4±0.2, 16.8±0.2, at about 22° C.

18. Crystalline P-1 form according to claim 16, which is characterized by a differential scanning calorimetry thermogram having an endothermic peak at about 217° C. to about 223° C., and an exotherm peak at about 222° C. to 225° C. followed by an endotherm peak at 255° C. to about 259° C.

19. Crystalline Form 0.5SBu-4 of crystalline 1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide, which is characterized by unit cell parameters substantially equal to the following:

| Cell dimensions: | a = 10.688(1) Å |
| | b = 15.006(2) Å |
| | c = 16.041(2) Å |
| | α = 85.51(1) |
| | β = 83.15(1) |
| | γ = 74.13(1) |
| Space group | P-1 |
| Molecules/asymmetric unit | 2 | wherein the crystalline form is at about +22° C.

20. Crystalline Form 0.5SBu-4 according to claim 19, which is characterized by fractional atomic coordinates substantially as listed in Table 5.

21. Crystalline Form 0.5SBu-4 according to claim 19, which is characterized by a powder X-ray diffraction pattern substantially in accordance with that shown in FIG. 6.

22. Crystalline Form 0.5SBu-4 according to claim 19, having a powder X-ray diffraction pattern comprising the following 2θ values (CuKα λ=1.5418 Å): 6.1±0.2, 8.1±0.2, 12.9±0.2, 13.4±0.2 and 18.5±0.2, at about 22° C.

* * * * *